(12) United States Patent
Klink et al.

(10) Patent No.: US 10,077,479 B2
(45) Date of Patent: Sep. 18, 2018

(54) FUSION GENE AS THERAPEUTIC TARGET IN PROLIFERATIVE DISEASES

(71) Applicant: Technische Universitat Dresden, Dresden (DE)

(72) Inventors: Barbara Klink, Dresden (DE); Khalil Abouelaradat, Dresden (DE); Evelin Schroeck, Dresden (DE)

(73) Assignee: Technische Universitat Dresden, Dresden (DE)

( * ) Notice: Subject to any disclaimer, the term of this patent is extended or adjusted under 35 U.S.C. 154(b) by 0 days.

(21) Appl. No.: 15/114,003

(22) PCT Filed: Jan. 22, 2015

(86) PCT No.: PCT/EP2015/051268
§ 371 (c)(1),
(2) Date: Jul. 25, 2016

(87) PCT Pub. No.: WO2015/110538
PCT Pub. Date: Jul. 30, 2015

(65) Prior Publication Data
US 2016/0340738 A1 Nov. 24, 2016

(30) Foreign Application Priority Data

Jan. 24, 2014 (EP) .................................. 14152417

(51) Int. Cl.
*G01N 33/574* (2006.01)
*C12Q 1/6886* (2018.01)
*C07K 14/47* (2006.01)
*C07K 16/40* (2006.01)
*C12Q 1/48* (2006.01)

(52) U.S. Cl.
CPC ........ *C12Q 1/6886* (2013.01); *C07K 14/4748* (2013.01); *C07K 16/40* (2013.01); *C12Q 1/485* (2013.01); *G01N 33/57407* (2013.01); *G01N 33/57484* (2013.01); *C07K 2319/00* (2013.01); *C12Q 2600/158* (2013.01); *G01N 2500/04* (2013.01)

(58) Field of Classification Search
None
See application file for complete search history.

(56) References Cited

U.S. PATENT DOCUMENTS

| 2007/0082337 A1 | 4/2007 | Sorek et al. |
| 2011/0195848 A1 | 8/2011 | Roopra et al. |
| 2013/0116132 A1 | 5/2013 | Sharma et al. |

OTHER PUBLICATIONS

Ballard et al., "A roundabout way to cancer," Advances in Cancer Research; Guidance Molecules in Cancer and Tumor Angiogenesis, 2012, vol. 114, pp. 187-235, Academic Press, US.
De La Mota-Peynado et al., "The Proteasome-associated protein Ecm29 inhibits proteasomal ATPase activity and in vivo protein degradation by the proteasome," Journal of Biological Chemistry, Aug. 30, 2013, vol. 288, No. 41, pp. 29467-29481.
Mullins et al., "Establishment and characterization of primary glioblastoma cell lines from fresh and frozen material: A detailed comparison," PLOS ONE, Aug. 2013, vol. 8, No. 8, p. e71070.
Sundaresan et al., "Dynamic expression patterns of Robo (Robo1 and Robo2) in the developing murine central nervous system," The Journal of Comparative Neurology, 2004, vol. 468, No. 4, pp. 467-481.
Yan et al., "IDH1 and IDH2 mutations in gliomas," New England Journal of Medicine, Feb. 19, 2009, vol. 360, No. 8, pp. 765-773.
Database Geneseq [Online] Nov. 8, 2012 "Gene for use in infectious/inflammatory state determination SEQ:1250", XP002738816, retrieved from EBI accession No. GSN:AZZ57732, Database accession No. AZZ57732.
Database Geneseq [Online] Jan. 5, 2012 "Human colorectal cancer diagnosing RNA SEQ:1131", XP002738817, retrieved from EBI accession No. GSN:AZP88647, Database accession No. AZP88647.
Database Geneseq [Online] Jul. 4, 2013 "Human DNA (ASSAY0628), SEQ ID 461", XP002738818, retrieved from EBI accession No. GSN:BA019542, Database accession No. BA019542.
Database Geneseq [Online] Oct. 29, 2009 "Human endogenous cell essential target cDNA sequence, SEQ: 1108.", XP002738819, retrieved from EBI accession No. GSN:AXQ62638, Database accession No. AXQ62638.

*Primary Examiner* — Catherine S Hibbert
(74) *Attorney, Agent, or Firm* — Olson & Cepuritis, Ltd.

(57) ABSTRACT

The present invention relates to a new fusion gene, KIAA0368-ROBO2, and the use thereof in methods for diagnosing cancer, in particular a glioblastoma in a subject, wherein the presence and/or expression of said fusion gene in a sample derived from said subject is determined, and wherein the presence or expression of said fusion gene is attributed to the presence of a glioblastoma in said patient. Also methods for the identification of compounds useful in the medical intervention of glioma, in particular glioblastoma, are provided. Accordingly, the present invention also relates to diagnostic means as well as to the medical intervention in cancer, like glioma and in particular glioblastoma. The invention further relates to the use of the fusion gene for diagnosing and/or monitoring of tumor progression, preferably of the progression of brain tumors, as well as for the subclassification of brain tumors and other proliferative diseases. The invention further provides a method for determining whether a subject suffering from a proliferative disease is susceptible to treatment with an inhibitor of the activity of the KIAA0368-ROBO2 fusion protein.

3 Claims, 12 Drawing Sheets
Specification includes a Sequence Listing.

Figure 5A

ATGACCTCACGGACAAAGCGAAGGCAGAAAGTTAAAATCAGCATATCGAAAATAAATCACTCTAGTTACC

GAAAAGAACATAGGCCGTTTTGGGAGCACCAGCCACCTCCACACCAGAACTGGGCTGTCGGGGGCCGCTG

CGGCGCAGGGGCTCGTCCGGGACTGAGTCAGCGCCGGGGCCGAGAAGTTCGGCGGGAGGCGCAGGGCGGG

GCTTCCTCCCGCCGACTCCGAGCCCGGCTCTACTTTTCTGAGTCCACGTCTCTTCCTTTGGACAGGCGTG

GCAGCCCGGGCCCGCTCGGCCCAGCCCCTCACGGACTGCGGCGCGCGGCTCCCCGGGGCCCGGCCCGCCG

AACGCCTCGCTCTACAGCCCTCACCTCGCGGCGCCGAGCGCAGCGTCCGCGGCATGGAGACCGGCTCCGA

CTCAGGTCAGAGGCCCGCCCCCGGGCCGCGGGGGACTGGCCCTGCGCGCGCGGCGGCGCGGTTAGGCCGG

GCCGCCCGCACAGGCCGCCGCGTGTCGAGTCCGCGCGGGGAGCGCACGCGGGGCGGGCGGCGACAGATCA

GCTTGAACGGGTCTTTTTACGACTTGGCCATGCTGAAACAGATGAACAATTACAGAATATTATATCTAAA

TTCCTTCCTCCTGTTTTGCTCAAACTCTCTAGCACCCAAGAAGGAGTACGTAAAAAGGTAATGGAACTGC

TGGTCCATCTGAATAAACGTATAAAAAGCCGCCCCAAAATACAACTTCCAGTAGAGACACTGTTGGTTCA

GTACCAGGACCCTGCTGCAGTTTCCTTTGTCACAAATTTTACTATAATTTATGTTAAAATGGGCTATCCT

CGCCTACCAGTGGAAAAACAATGTGAACTGGCCCCTACGCTTCTTACTGCCATGGAAGGGAAGCCTCAGC

CACAGCAGGATAGCTTAATGCATCTTTTAATACCAACCCTTTTTCACATGAAATACCCTGTTGAATCATC

AAAATCAGCTTCTCCATTTAATCTTGCTGAGAAACCAAAGACTGTGCAGCTGCTTTTGGACTTCATGCTA

GATGTCCTTCTGATGCCTTATGGTTACGTGTTAAATGAATCCCAGAGTCGCCAAAATTCATCTTCAGCAC

AGGGTTCTTCTTCAAACAGTGGCGGAGGTTCTGGAATCCCACAGCCTCCTCCGGGAATGAGCTTTTATGC

AGCCAAACGAGTTATTGGTGATAACCCATGGACACCTGAACAATTGGAACAGTGCAAATTGGGAATCGTG

AAATTCATAGAAGCTGAACAGGTGCCTGAACTTGAAGCTGTTCTCCACTTGGTGATTGCCTCTAGTGATA

CACGCCACAGTGTGGCAACGGCAGCAGACCTGGAATTGAAAAGCAAACAGAGCTTAATTGACTGGAATAA

TCCTGCCATCATTAATAAGATGTACAAGGTGTACCTTGGAGATATACCACTGAAGACAAAAGAGGGTGCA

GTTCTGAAGCCAGAGTTGAAAAGGGACCCTGTCAGTACAAGAGTCAAGTTAAAGATTGTCCCCCATCTCC

TCCGCTCTAGACAAGCTGCTGAAACGTTCCCAGCCAACATTCAGGTGGTGTATGATGGACTTTTTGGTAC

Figure 5A (continued)

AAATACAAATTCAAAGTTAAGAACATTATCCCTGCAATTTGTGCATCATATTTGTATAACCTGTCCAGAA

ATCAAGATTAAGCCATTAGGTCCAATGCTTTTGAATGGCCTCACCAAGCTAATCAATGAATACAAAGAGG

ACCCTAAACTACTGTCAATGGCATATTCAGCTGTTGGAAAACTCTCCAGTCGGATGCCACATTTATTCAC

TAAGGATATAGCGCTTGTGCAGCAGCTTTTTGAAGCCCTTTGCAAGGAAGAGCCTGAGACTCGACTTGCT

ATTCAAGAAGCTTTATCTATGATGGTTGGAGCGTATAGTACTTTGGAAGGGGCACAGCGAACTCTCATGG

AGGCACTTGTGGCTTCGTACTTAATAAAGCCTGAAGTTCAAGTTCGACAAGTGGCTGTGAAATTTGCCAG

TACGGTGTTTCCCTCAGATCATATCCCTTCCAGATATTTGCTGCTACTGGCTGCAGGAGATCCACGTGAA

GAAGTTCATGGAGAAGCACAACGCGTATTAAGGTGTCTTCCAGGTAGAAACAGAAAAGAAAGTACTTCTG

AGCAGATGCCTTCCTTCCCAGAAATGGTTTATTACATCCAAGAAAAGGCTTCTCATCGAATGAAAACTCC

AGTCAAGTACATGACCGGGACCACTGTCCTTCCATTTAACCCAGCAGCCTTTGGAGAGATCGTTCTGTAC

TTGCGCATGTGCCTTGCGCACAGTGCGGGGTGGTGCCCACCTCTCAGAGTTTGGCTGATATGCAGGATC

ATGCCCCAGCCATTGGGCGCTACATACGGACTTTAATGTCAAGCGGGCAGATGGCACCCTCATCATCTAA

CAAGAGTGGGGAGACTAACCCTGTCCAGATCTACATTGGCCTGCTTCAGCAGCTGTTAGCAGGTGTTGGA

GGTTTGCCGGTTATGTACTGTCTATTGGAAGCTGTGTCAGTGTATCCAGAAAAGCTGGCTACCAAATTTG

TAGACAAAACAGAATGGATAAAGAGTCTGATGAATAACAGTAAAGAAGAAATGCGCGAACTGGCAGCGTT

GTTTTATTCTGTAGTGGTATCAACAGTGTCGGGGAATGAGTTGAAATCAATGATAGAACAGCTTATAAAG

ACTACAAAAGACAATCACAGCCCGGAGATACAGCATGGATCCTTGCTTGCATTGGGATTCACGGTGGGAA

GGTATTTGGCTAAAAAGAAAATGAGAATGTCAGAGCAACAAGACCTGGAGAGAAATGCTGACACCCTCCC

TGATCAAGAGGAACTCATTCAGAGTGCTACAGAAACAATAGGCTCATTTTTGGACAGTACATCACCCCTC

CTGGCAATTGCTGCCTGCACAGCCCTGGGTGAAATTGGCAGAAATGGTCCACTTCCAATCCCCAGTGAGG

GATCTGGCTTTACCAAATTGCATCTTGTAGAAAGCTTACTAAGTAGAATACCTTCCAGTAAAGAAACAAA

TAAGATGAAAGAACGAGCAATCCAAACACTGGGATATTTTCCAGTTGGGGATGGAGATTTTCCTCACCAG

AAACTCCTCTTGCAAGGTCTGATGGATTCTGTGGAGGCCAAGCAGATAGAACTTCAGTTCACTATTGGCG

AAGCCATTACCAGTGCTGCAATAGGAACTAGTTCTGTGGCTGCCCGAGATGCCTGGCAAATGACTGAAGA

GGAATATACTCCACCTGCTG

Figure 5A (continued)

TGTTACGAGATGACTTCCGACAAAACCCCACA

GATGTTGTAGTGGCAGCTGGAGAGCCTGCAATCCTGGAGTGCCAGCCTCCCCGGGGACACCCAGAACCCA

CCATCTACTGGAAAAAAGACAAAGTTCGAATTGATGACAAGGAAGAAAGAATAAGTATCCGTGGTGGAAA

ACTGATGATCTCCAATACCAGGAAAAGTGATGCAGGGATGTATACTTGTGTTGGTACCAATATGGTGGGA

GAAAGGGACAGTGACCCAGCAGAGCTGACTGTCTTTGAACGACCCACATTTCTCAGGAGGCCAATTAACC

AGGTGGTACTGGAGGAAGAAGCTGTAGAATTTCGTTGTCAAGTCCAAGGAGATCCTCAACCAACTGTGAG

GTGGAAAAAGGATGATGCAGACTTGCCAAGAGGAAGGTATGACATCAAAGACGATTACACACTAAGAATT

AAAAAGACCATGAGTACAGATGAAGGCACCTATATGTGTATTGCTGAGAATCGGGTTGGAAAAATGGAAG

CCTCTGCTACACTCACCGTCCGAGCTCCCCACAGTTTGTGGTTCGGCCAAGAGATCAGATTGTTGCTCA

AGGTCGAACAGTGACATTTCCCTGTGAAACTAAAGGAAACCCACAGCCAGCTGTTTTTTGGCAGAAAGAA

GGCAGCCAGAACCTACTTTTCCCAAACCAACCCCAGCAGCCCAACAGTAGATGCTCAGTGTCACCAACTG

GAGACCTCACAATCACCAACATTCAACGTTCCGACGCGGGTTACTACATCTGCCAGGCTTTAACTGTGGC

AGGAAGCATTTTAGCAAAAGCTCAACTGGAGGTTACTGATGTTTTGACAGATAGACCTCCACCTATAATT

CTACAAGGCCCAGCCAACCAAACGCTGGCAGTGGATGGTACAGCGTTACTGAAATGTAAAGCCACTGGTG

ATCCTCTTCCTGTAATTAGCTGGTTAAAGGAGGGATTTACTTTTCCGGGTAGAGATCCAAGAGCAACAAT

TCAAGAGCAAGGCACACTGCAGATTAAGAATTTACGGATTTCTGATACTGGCACTTATACTTGTGTGGCT

ACAAGTTCAAGTGGAGAGACTTCCTGGAGTGCAGTGCTGGATGTGACAGAGTCTGGAGCAACAATCAGTA

AAAACTATGATTTAAGTGACCTGCCAGGGCCACCATCCAAACCGCAGGTCACTGATGTTACTAAGAACAG

TGTCACCTTGTCCTGGCAGCCAGGTACCCCTGGAACCCTTCCAGCAAGTGCATATATCATTGAGGCTTTC

AGCCAATCAGTGAGCAACAGCTGGCAGACCGTGGCAAACCATGTAAAGACCACCCTCTATACTGTAAGAG

GACTGCGGCCCAATACAATCTACTTATTCATGGTCAGAGCGATCAACCCCAAGGTCTCAGTGACCCAAG

TCCCATGTCAGATCCTGTGCGCACACAAGATATCAGCCCACCAGCACAAGGAGTGGACCACAGGCAAGTG

CAGAAAGAGCTAGGAGATGTCCTTGTCCGTCTTCATAATCCAGTTGTGCTGACTCCCACCACGGTTCAGG

TCACATGGACGGTTGATCGCCAACCCCAGTTTATCCAAGGCTACCGAGTGATGTATCGTCAGACTTCAGG

TCTGCAGGCGACATCTTCGTGGCAGAATTTAGATGCCAAAGTCCCGACTGAACGAAGTGCTGTCTTAGTC

Figure 5A (continued)

AACCTGAAAAAGGGGGTGACTTATGAAATTAAAGTACGGCCATATTTTAATGAGTTCCAAGGAATGGATA

GTGAATCTAAAACGGTTCGTACTACTGAAGAAGCCCCAAGTGCCCCACCACAGTCTGTCACTGTACTGAC

AGTTGGAAGCTACAATAGCACAAGTATTAGTGTTTCCTGGGATCCTCCTCCTCCAGATCACCAGAATGGA

ATTATCCAAGAATACAAGATCTGGTGTCTAGGAAATGAAACGCGATTCCATATCAACAAAACTGTGGATG

CAGCCATTCGGTCCGTAATAATTGGTGGATTATTCCCAGGTATTCAATACCGGGTAGAGGTTGCAGCTAG

TACCAGTGCAGGGGTTGGAGTAAAGAGTGAGCCACAGCCAATAATAATCGGGAGACGCAATGAAGTTGTC

ATTACTGAAAACAATAACAGCATAACTGAGCAAATCACTGATGTGGTGAAGCAACCAGCCTTTATAGCTG

GTATTGGTGGTGCCTGCTGGGTAATTCTGATGGGTTTTAGCATATGGTTGTATTGGCGAAGAAAGAAGAG

GAAGGGACTCAGTAATTATGCTGTTACGTTTCAAAGAGGAGATGGAGGACTAATGAGCAATGGAAGCCGT

CCAGGTCTTCTCAATGCTGGTGATCCCAGCTATCCATGGCTTGCTGATTCTTGGCCAGCCACGAGCTTGC

CAGTAAATAATAGCAACAGTGGCCCAAATGAGATTGGAAATTTTGGCCGTGGAGATGTGCTGCCACCAGT

TCCAGGCCAAGGGGATAAAACAGCAACGATGCTCTCAGATGGAGCCATTTATAGTAGCATTGACTTCACT

ACCAAAACCAGTTACAACAGTTCCAGCCAAATAACACAGGCTACCCCATATGCCACGACACAGATCTTGC

ATTCCAACAGCATACATGAATTGGCTGTCGATCTGCCTGATCCACAATGGAAAAGCTCAATTCAGCAAAA

AACAGATCTGATGGGATTTGGTTATTCTCTACCTGATCAGAACAAAGGTAACAATGGTGGGAAAGGTGGA

AAAAAGAAGAAAAATAAAAACTCTTCTAAACCACAGAAAAACAATGGATCCACTTGGGCCAATGTCCCTC

TACCTCCCCCCCCAGTCCAGCCCCTTCCTGGCACGGAGCTGGAACACTATGCAGTGGAACAACAAGAAAA

TGGCTATGACAGTGATAGCTGGTGCCCACCATTGCCAGTACAAACTTACTTACACCAAGGTCTGGAAGAT

GAACTGGAAGAAGATGATGATAGGGTCCCAACACCTCCTGTTCGAGGCGTGGCTTCTTCTCCTGCTATCT

CCTTTGGACAGCAGTCCACTGCAACTCTTACTCCATCCCCACGGGAAGAGATGCAACCCATGCTGCAGGC

TCACCTGGATGAGTTGACAAGAGCCTATCAGTTTGATATAGCAAAACAAACATGGCACATTCAAAGCAAT

AATCAACCTCCACAGCCTCCAGTTCCACCGTTAGGTTATGTGTCTGGAGCCTTGATTTCTGATTTGGAAA

CGGATGTTGCAGATGATGATGCCGACGACGAAGAGGAAGCTTTAGAAATCCCCAGGCCCCTGAGAGCACT

GGACCAGACTCCTGGATCCAGCATGGACAATCTAGACAGCTCTGTGACAGGAAAAGCCTTTACCTCCTCT

CAAAGACCTCGACCTACCAGCCCATTTTCTACTGACAGTAACACCAGTGCAGCCCTGAGTCAAAGTCAGA

Figure 5A (continued)

GGCCTCGGCCCACTAAAAAACACAAGGGAGGGCGGATGGACCAACAACCAGCATTGCCTCATCGAAGGGA

AGGAATGACAGATGAGGAGGCCTTGGTGCCCTATAGCAAGCCCAGTTTCCCATCTCCAGGTGGCCACAGC

TCATCAGGAACAGCTTCTTCTAAGGGATCCACTGGACCTAGGAAAACCGAGGTGTTGAGAGCAGGCCACC

AGCGCAATGCCAGCGACCTTCTTGACATAGGATATATGGGCTCCAACAGTCAAGGACAGTTTACAGGTGA

ATTATAG

Figure 5B

MTSRTKRRQKVKISISKINHSSYRKEHRPFWEHQPPPHQNWAVGGRCGAGARPGLSQRRGRE
VRREAQGGASSRRLRARLYFSESTSLPLDRRGSPGPLGPAPHGLRRAAPRGPARRTPRSTAL
TSRRRAQRPRHGDRLRLRSEARPRAAGDWPCARGGAVRPGRPHRPPRVESARGAHAGRAATD
QLERVFLRLGHAETDEQLQNIISKFLPPVLLKLSSTQEGVRKKVMELLVHLNKRIKSRPKIQ
LPVETLLVQYQDPAAVSFVTNFTIIYVKMGYPRLPVEKQCELAPTLLTAMEGKPQPQQDSLM
HLLIPTLFHMKYPVESSKSASPFNLAEKPKTVQLLLDFMLDVLLMPYGYVLNESQSRQNSSS
AQGSSSNSGGGSGIPQPPPGMSFYAAKRVIGDNPWTPEQLEQCKLGIVKFIEAEQVPELEAV
LHLVIASSDTRHSVATAADLELKSKQSLIDWNNPAIINKMYKVYLGDIPLKTKEGAVLKPEL
KRDPVSTRVKLKIVPHLLRSRQAAETFPANIQVVYDGLFGTNTNSKLRTLSLQFVHHICITC
PEIKIKPLGPMLLNGLTKLINEYKEDPKLLSMAYSAVGKLSSRMPHLFTKDIALVQQLFEAL
CKEEPETRLAIQEALSMMVGAYSTLEGAQRTLMEALVASYLIKPEVQVRQVAVKFASTVFPS
DHIPSRYLLLLAAGDPREEVHGEAQRVLRCLPGRNRKESTSEQMPSFPEMVYYIQEKASHRM
KTPVKYMTGTTVLPFNPAAFGEIVLYLRMCLAHSAGVVPTSQSLADMQDHAPAIGRYIRTLM
SSGQMAPSSSNKSGETNPVQIYIGLLQQLLAGVGGLPVMYCLLEAVSVYPEKLATKFVDKTE
WIKSLMNNSKEEMRELAALFYSVVVSTVSGNELKSMIEQLIKTTKDNHSPEIQHGSLLALGF
TVGRYLAKKKMRMSEQQDLERNADTLPDQEELIQSATETIGSFLDSTSPLLAIAACTALGEI
GRNGPLPIPSEGSGFTKLHLVESLLSRIPSSKETNKMKERAIQTLGYFPVGDGDFPHQKLLL
QGLMDSVEAKQIELQFTIGEAITSAAIGTSSVAARDAWQMTEEEYTPPAVLRDDFRQNPTDV
VVAAGEPAILECQPPRGHPEPTIYWKKDKVRIDDKEERISIRGGKLMISNTRKSDAGMYTCV
GTNMVGERDSDPAELTVFERPTFLRRPINQVVLEEEAVEFRCQVQGDPQPTVRWKKDDADLP
RGRYDIKDDYTLRIKKTMSTDEGTYMCIAENRVGKMEASATLTVRAPPQFVVRPRDQIVAQG
RTVTFPCETKGNPQPAVFWQKEGSQNLLFPNQPQQPNSRCSVSPTGDLTITNIQRSDAGYYI
CQALTVAGSILAKAQLEVTDVLTDRPPPIILQGPANQTLAVDGTALLKCKATGDPLPVISWL
KEGFTFPGRDPRATIQEQGTLQIKNLRISDTGTYTCVATSSSGETSWSAVLDVTESGATISK
NYDLSDLPGPPSKPQVTDVTKNSVTLSWQPGTPGTLPASAYIIEAFSQSVSNSWQTVANHVK
TTLYTVRGLRPNTIYLFMVRAINPQGLSDPSPMSDPVRTQDISPPAQGVDHRQVQKELGDVL
VRLHNPVVLTPTTVQVTWTVDRQPQFIQGYRVMYRQTSGLQATSSWQNLDAKVPTERSAVLV
NLKKGVTYEIKVRPYFNEFQGMDSESKTVRTTEEAPSAPPQSVTVLTVGSYNSTSISVSWDP
PPPDHQNGIIQEYKIWCLGNETRFHINKTVDAAIRSVIIGGLFPGIQYRVEVAASTSAGVGV
KSEPQPIIIGRRNEVVITENNNSITEQITDVVKQPAFIAGIGGACWVILMGFSIWLYWRRKK
RKGLSNYAVTFQRGDGGLMSNGSRPGLLNAGDPSYPWLADSWPATSLPVNNSNSGPNEIGNF
GRGDVLPPVPGQGDKTATMLSDGAIYSSIDFTTKTSYNSSSQITQATPYATTQILHSNSIHE
LAVDLPDPQWKSSIQQKTDLMGFGYSLPDQNKGNNGGKGGKKKKNKNSSKPQKNNGSTWANV

Figure 5B (continued)

PLPPPPVQPLPGTELEHYAVEQQENGYDSDSWCPPLPVQTYLHQGLEDELEEDDDRVPTPPV

RGVASSPAISFGQQSTATLTPSPREEMQPMLQAHLDELTRAYQFDIAKQTWHIQSNNQPPQP

PVPPLGYVSGALISDLETDVADDDADDEEEALEIPRPLRALDQTPGSSMDNLDSSVTGKAFT

SSQRPRPTSPFSTDSNTSAALSQSQRPRPTKKHKGGRMDQQPALPHRREGMTDEEALVPYSK

PSFPSPGGHSSSGTASSKGSTGPRKTEVLRAGHQRNASDLLDIGYMGSNSQGQFTGEL

FUSION GENE AS THERAPEUTIC TARGET IN PROLIFERATIVE DISEASES

CROSS-REFERENCE TO RELATED APPLICATIONS

This application is a U.S. National Stage of PCT/EP2015/051268, filed Jan. 22, 2015, which claims priority of European Patent Application No. 14 152 417.3, filed Jan. 24, 2014, both incorporated herein by reference.

FIELD OF THE INVENTION

The present invention relates to a new fusion gene, KIAA0368-ROBO2, and the use thereof in methods for diagnosing cancer, in particular a glioblastoma in a subject, wherein the presence and/or expression of said fusion gene in a sample derived from said subject is determined, and wherein the presence or expression of said fusion gene is attributed to the presence of a glioblastoma in said patient. Also, methods for the identification of compounds useful in the medical intervention of glioma, in particular glioblastoma, are provided. Accordingly, the present invention also relates to diagnostic means as well as to the medical intervention in cancer, like glioma and in particular glioblastoma. The invention further relates to the use of the fusion gene for diagnosing and/or monitoring of tumor progression, preferably of the progression of brain tumors, as well as for the subclassification of brain tumors and other proliferative diseases. The invention further provides a method for determining whether a subject suffering from a proliferative diseases is susceptible to treatment with an inhibitor of the activity of the KIAA0368-ROBO2 fusion protein.

SEQUENCE LISTING INCORPORATION

Biological sequence information for this application is included in an ASCII text file, filed with the application, having the file name "MAI206SEQ.txt", created on Jul. 25, 2016, and having a file size of 40,344 bytes, which is incorporated herein by reference.

BACKGROUND OF THE INVENTION

Gliomas, the most common adult-onset neurological neoplasm, encompass a family of primary central nervous system tumors including glioblastoma, astrocytoma, oligodendroglioma, and ependymoma, along with the juvenile onset neoplasms such as juvenile pilocystic astrocytoma.

Malignant gliomas are typically characterized by overexpression of growth factors/tumor associated antigens believed to significantly contribute to the unchecked growth of such tumors. Various malignant gliomas, such as glioblastomas, exhibit epidermal growth factor receptor (EGFR) overexpression leading to increased aggressiveness and poor prognosis. Malignant gliomas may also display over-expression of platelet-derived growth factor receptor, a phenomenon which has also been correlated with increased malignancy and poor prognosis.

Malignant gliomas (WHO grade III-IV), the most common type of primary brain tumors, are aggressive, highly invasive, and neurologically destructive tumors, which are among the deadliest of all human cancers. Of the estimated 17,000 new brain tumors diagnosed each year in the United States, about half are malignant gliomas. Malignant glioma cells produce very invasive brain tumors with infiltration of both white and gray matter. At the time of diagnosis, microscopic extension through much of the neural axis by malignant glioma is the rule. Such extension by motile invading cells underlies the incurability by surgery of most gliomas, even when they appear small and restricted in nature.

Glioblastoma (GBM) (WHO grade IV), the most serious form of malignant glioma, are extremely aggressive brain tumors which generally arise in the upper brain (cerebrum), but which may also occur elsewhere in the central nervous system, such as in the spinal cord, cerebellum, brain stem, or optic chiasm. Low-grade gliomas (WHO grade I-II), which include astrocytomas, oligodendrogliomas, and pilocytic astrocytomas, account for 25% of all primary brain tumors, and over time most of these low-grade tumors dedifferentiate into more malignant gliomas. Diffuse astrocytomas are predominantly located in the cerebral hemispheres of adults and have an inherent tendency to progress to anaplastic astrocytoma (WHO grade III) and (secondary) glioblastoma (WHO grade IV). The majority of glioblastomas develop de novo (primary glioblastomas), without an identifiable less-malignant precursor lesion.

Glioblastoma is the most common and aggressive primary brain tumor in adults. Its prognosis remains extremely poor, despite multimodal treatment by surgery, radiotherapy and chemotherapy (Wen et al, N Engl J Med 2008, 359: 492-507). The median survival of patients with glioblastomas is only 12-15 months. When these tumors recur, conventional salvage therapies produce minimal benefit, with only 8-15% of patients alive and free from progression at 6 months (6M-PFS). These tumors are now well characterized at the transcriptome and genome levels. Several studies have demonstrated that a combination of these two molecular levels may be advantageous for determining robust signatures and clinically relevant molecular classifiers of glioblastoma (de Tayrac et al, Genes Chromosomes Cancer 2009, 48: 55-68; Nigro et al, Cancer Res, 2005, 65: 1678-1686).

The Gold standard for the diagnostics of gliomas is by histopathological and immunohistochemical examination by a neuropathologist according to the WHO classification of central nervous systems (D. N. Louis, H. Ohgaki, O. D. Wiestler and W. K. Cavenee, ed., International Agency for Research on Cancer (IARC) Press, Lyon, 2007). The World Health Organization (WHO) classification divides gliomas into three main subgroups: astrocytomas, oligodendrogliomas, and mixed gliomas (oligoastrocytomas). It further distinguishes between four malignancy grades (WHO grades I-IV). Because phenotypic heterogeneity within these tumors is quite frequent, the histopathologic examination yields differing results, even when performed by experienced neuropathologists. Especially the differentiation between glioblastoma multiforme (WHO grade IV) and anaplastic glioma (WHO grade III) with either oligodendroglial, astrocytic or both features could be very difficult. Moreover, the clinical outcome is often not predictable, which may reflect biological heterogeneity within each of the tumor groups. Research during the last decades has thus been focused on a more accurate characterization of these tumors including the identification of new prognostic markers in order to supply and complement histology-based classification.

A few clinically-relevant biomarkers have been identified so far in glioblastoma. The somatic mutation affecting amino acid 132 of the isocitrate dehydrogenase 1 (IDH1) protein is an independent prognostic biomarker associated with better clinical outcome in gliomas, including glioblastoma (Ichimura et al, Neuro Oncol, 2009, 11: 341-347; Yan et al, N Engl J Med, 2009, 360: 765-773), but this mutation is rare in glioblastoma (around 6%) and concerns almost exclusively secondary glioblastomas (Sanson et al, J Clin Oncol, 2009, 274150-4154). Changes in promoter DNA methylation pattern of genes involved in key biological pathways have been reported in glioblastoma. For instance, the retinoblastoma (RB), the PI3K and p53 pathways are affected by CpG island promoter hypermethylation (RB, CDKN2A, PTEN, TP53) (Watanabe et al, J Neuropathol Exp Neurol, 2001, 60: 1181-1189; Nakamura et al., Lab Invest, 2001, 81: 77-82; Costello et al, Cancer Res, 1996, 56: 2405-2410; Bello et al, Cancer Genet Cytogenet, 2006, 164: 172-173; Amatya et al, Acta Neuropathol, 2005, 110: 178-184).

In some cancers, chromosomal rearrangements (created when chromosomes break and then recombine incorrectly) may create fusion genes where parts of two genes combine together so that the latter part of a certain gene falls under the control of the promoter of another. This can lead to either over-activation of a certain proto-oncogene (a gene whose over-expression contributes to carcinogenesis; these are usually involved in cellular growth and proliferation) or abolishment of the function of a tumor suppressor gene. The most famous example is the fusion of bcr and c-abl in chronic myelogenic leukemia (CML) and less frequently in acute lymphoblastic leukemia (ALL) which is created from the fusion of parts of chromosomes 9 and 22. This fusion causes an over expression of the proto-oncogene c-Abl which in turn leads to an acceleration of cell proliferation. These fusion genes create lucrative therapy targets as they are specific to tumor cells and therefore, understanding their function is imperative to creating new therapies (reviewed in: Yeung and Hughes (2012) Therapeutic targeting of BCR-ABL: prognostic markers of response and resistance mechanism in chronic myeloid leukemia. *Crit. Rev. Oncog.* 17: 17-30; Wong S F and Mirshahidi H (2011) Use of tyrosine kinase inhibitors for chronic myeloid leukemia: management of patients and practical applications for pharmacy practitioners. *Ann. Pharmacother.* 45: 787-797.).

Multifocal glioblastomas are especially aggressive cases of glioblastoma (GBM) where multiple tumors are found in the brain of the patient. These cancers form around 10% of diagnosed GBM cases and their cause is not fully understood. It can be assumed that these tumors have an especially invasive nature with an enhanced ability to transplant in other regions of the brain. Treatment of brain cancers is not easy or very effective; remission rates remain high. Surgery is hampered by the fact that GBM cells are highly infiltrative and the surgeon doesn't have the option of removing normal tissue around the tumor. In addition, populations of GBM cells are radio- and chemoresistant making radio- and chemotherapy not completely efficient. Furthermore, treatment success is increasingly found to depend on the proper diagnosis and molecular classification.

Accordingly, there is a great need for better molecular markers, in particular for the diagnosis and treatment of GBM.

Roundabout (Robo) 2 is a single-pass transmembrane receptor which functionally resembles receptor tyrosine kinases (RTK). It is a member of a family of four such receptors (Robo1-4) that bind to their ligands, members of the Slit family. This binding is mediated by the first two Ig-like domains in the extracellular part of the Robo receptor. The Robo-Slit signaling has been reported to be important for axon guidance in neurons and for migration of glial cells and thus can be thought to be important for migration and invasion, two features of aggressive cancers. However, the Robo-Slit pathway is now found to play a role in other cellular phenomena. For example, Robo receptors are reported to be involved in the proper differentiation and localization of neuronal progenitor cells. Deletion of Robo2 inhibited the differentiation of these cells into glial cells and their proper localization in the subventricular zone (SVZ). Robo signaling was also found to be important for the maintenance of the stem cell population in the intestinal crypt.

Roundabout 2 (Robo2) is a member of the Roundabout family of receptors which includes Robo1-4. The focus of these receptors has been on their role in axonal guidance and adhesion; however, their role in stem cell maintenance and differentiation is emerging (Zhou, W J et al. Nature, 2013, 501: 107-113; Borrell, V et al. Neuron, 2012, 76: 338-352). Therefore, it is expected that Slit-Robo aberrant signaling would play a role in tumorigenesis. The role of Slit-Robo signaling has been recently reported in pancreatic cancer (Tang et al., Carcinogenesis, 2014, [Epub ahead of print]), ovarian cancer (Dickinson et al., PLoS One, 2011, 6(11): e27792), melanoma (Denk et al, Int J Mol Med, 2011, 28:721-6), squamous cell carcinoma (Bauer et al., Carcinogenesis, 2011, 32:935-43), hepatocellular carcinoma (Avci, M E et al., BMC Cancer, 2008, 29: 392-403), colorectal carcinoma (Zhou W J et al., Cell Res., 2011, 21: 609-626), and indeed in epithelial tumors in general (Ballard and Hinck, Adv Cancer Res, 2012, 114:187-235). Furthermore, the pathway has been associated with angiogenesis (Ballard and Hinck, Adv Cancer Res, 2012, 114:187-235; Yang, X M et al., Biochem Biophys Res Commun, 2010, 28: 396).

KIAA0368 (otherwise known as ECM29) is a protein made up of several HEAT domains. It's described in the literature as an adaptor protein, mostly involved in binding to the 26S proteasome and aiding in its proper assembly and transport by linking it to motor proteins and several cellular compartments such as the ER and Golgi apparatus (Gorbea C et al., J Biol. Chem., 2010, 285: 31616-31633).

SUMMARY OF THE INVENTION

The present invention provides a novel and so far unknown fusion gene comprising fragments of the ROBO2 and KIAA0368 genes. The invention further provides a KIAA0368-ROBO2 fusion protein resulting from the expression of the novel fusion gene.

The KIAA0368-ROBO2 fusion gene and/or the KIAA0368-ROBO2 fusion protein play a role in the development of proliferative diseases, i.e. cancer. Such cancer or proliferative disease is in particular a glioma, and more specifically glioblastoma (GBM).

The present invention further provides simple methods for the detection of the transcript of the fusion gene, e.g. by using PCR. In addition, the invention provides simple methods for the detection of the KIAA0368-ROBO2 fusion protein in biological samples of a subject. These methods allow the simple screening of GBMs for the presence of the KIAA0368-ROBO2 fusion gene and/or transcript and/or fusion protein.

In a further embodiment, the present invention relates to use of the KIAA0368-ROBO2 fusion gene and/or transcript and/or fusion protein in methods for diagnosing proliferative diseases, i.e. cancer, such as glioma, and more specifically GBM.

Based on the KIAA0368-ROBO2 fusion gene and/or transcript and/or fusion protein, improved methods for diagnosing brain tumors and in particular glioma, are provided.

The KIAA0368-ROBO2 fusion gene and/or transcript and/or fusion protein is in particular suitable for diagnosing and/monitoring of tumor progression, most preferably of progression of brain tumors. Accordingly, ROBO2 and/or the KIAA0368-ROBO2 fusion gene and/or transcript and/or fusion protein is provided as a novel diagnostic marker for subclassification of brain tumors and other cancers.

The KIAA0368-ROBO2 fusion gene and/or fusion protein of the invention provide a novel therapeutic target for combatting proliferative diseases, i.e. cancer, such as glioma, and more specifically GBM. Accordingly, the invention further relates to agents, for example therapeutic antibodies, small molecule inhibitors etc. are provided, which are suitable for use in methods of treating said proliferative diseases. The KIAA0368-ROBO2 fusion gene and/or fusion protein thus enable novel specific, i.e. targeted therapies of cancer, in particular targeted therapies of gliomas using ROBO2 related targets. Thus, in a preferred embodiment, the invention relates to the ROBO2 dependent targeted therapy of gliomas.

The invention further provides recombinant polynucleotide molecules comprising the nucleic acid of the KIAA0368-ROBO2 fusion gene plus expression-controlling elements operably linked with said nucleic acid to drive expression thereof. In particular, the invention provides expression vectors comprising the nucleic acid of the KIAA0368-ROBO2 fusion gene. Said expression vector encoding a KIAA0368-ROBO2 fusion protein may be present in a compatible host cell. Moreover, said host cells may be used in processes for producing KIAA0368-ROBO2 fusion protein.

ROBO2 and accordingly the KIAA0368-ROBO2 fusion protein have the enzymatic activity of a tyrosine kinase. The invention further provides a screening method for compounds that are capable of inhibiting tyrosine kinase activity of a KIAA0368-ROBO2 fusion protein. Said compounds may be further used in the diagnostic and therapeutic methods of the present invention.

In a further embodiment, the present invention provides a kit for diagnosing a proliferative disease, specifically a glioma, more specifically GBM. Said kit is also suitable for diagnosing and/or monitoring of tumor progression, most preferably of the progression of brain tumors. Said kit is especially useful in the subclassification of brain tumors and other cancers.

The present invention further relates to a method for determining whether a subject suffering from a proliferative disease is susceptible to treatment with a tyrosine kinase inhibitor, preferably an inhibitor of ROBO2 kinase activity comprising detecting the expression of a KIAA0368-ROBO2 fusion protein in biological sample of said subject, wherein an elevated amount of a KIAA0368-ROBO2 fusion protein indicates that said subject is susceptible to treatment with a tyrosine kinase inhibitor.

BRIEF DESCRIPTION OF THE DRAWINGS

FIG. 5 shows the nucleic acid sequence, SEQ ID NO: 2 (FIG. 5A), and amino acid sequence, SEQ ID NO: 1 (FIG. 5B), of the KIAA0368-ROBO2 fusion gene. The non-underlined parts belong to the proportion of KIAA0368 and the underlined parts indicate the ROBO2 proportion. In the amino acid sequence (FIG. 5B), capital bold letter V refers to valine which was created from a codon formed from parts of KIAA0368 and ROBO2.

DETAILED DESCRIPTION OF THE INVENTION

Figure 1:
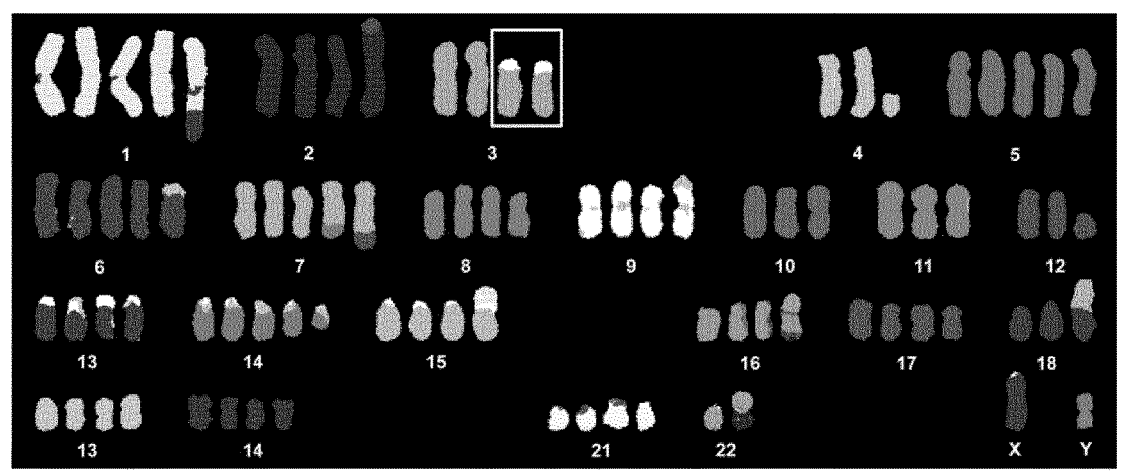
FIG. 1 shows the results of Spectral Karyotyping (SKY) on GBM Focus 1. Representative karyotype of the glioblastoma is given. Each chromosome (autosomes 1-22, X and Y) is marked with a different color displayed in different shades of grey. The cell line is near tetraploid in this case. White frame indicates the derivative chromosome der(3;9) due to a translocation between chromosomes 3 and 9 where a part of chromosome 9 (lighter area) is fused to a part of chromosome 3 (lower part).

The present invention generally relates to the following items:

1. A nucleic acid encoding a KIAA0368-ROBO2 fusion protein.

2. The nucleic acid of item 1, encoding a sequence at least 70% identical to the amino acid sequence of a fusion protein of KIAA0368-ROBO2 (SEQ ID NO. 1).

3. The nucleic acid of item 1 comprising a sequence at least 70% identical to the nucleic acid sequence of a fusion gene of KIAA0368-ROBO2 (SEQ ID NO. 2).

4. A polypeptide, which is a fusion protein of parts of KIAA0368 and ROBO2.

5. The polypeptide of item 4, having an amino acid sequence with at least 70% identity to the sequence of a fusion protein of KIAA0368-ROBO2 (SEQ ID NO: 1).

6. A method for diagnosing a proliferative disease in a subject comprising the steps of:
   determining the presence and/or expression of a fusion gene of KIAA0368-ROBO2 in a biological sample derived from said patient; and
   attributing the presence or expression of said fusion gene to the presence of a proliferative disease in said patient.

7. The method of item 6, wherein the presence and/or expression of said fusion gene is detected by a hybridisation and/or an amplification assay.

8. The method according to item 6, wherein the hybridisation and/or amplification assay is selected from the group consisting of polymerase chain reaction (PCR), real-time PCR, reverse transcriptase PCR (RT-PCR), fluorescent in situ hybridisation (FISH), chromogenic in situ hybridisation (CISH), break-apart in situ hybridisation (ba-FISH), and silver in situ hybridisation (SISH).

9. The method according to any one of items 6 to 8, wherein said fusion gene comprises one or more nucleotide sequences of a fragment of a gene, said fragment having a sequence with at least 70% identity to a sequence selected from the KIAA0368 (SEQ ID NO. 3) gene and the ROBO2 (SEQ ID 4) gene.

10. A method for diagnosing of proliferative diseases in a subject comprising the steps of
   determining the amount of at least one fusion protein of KIAA0368-ROBO2 in a biological sample; and
   comparing the detected amount of said fusion protein in the biological sample with an amount of a KIAA0368-ROBO2 fusion protein and/or a ROBO2 protein and/or a KIAA0368 protein characteristic of a normal control subject;
wherein an elevated amount of said at least one KIAA0368-ROBO2 fusion protein in said biological sample relative to the amount of said KIAA0368-ROBO2 fusion protein and/or a ROBO2 protein and/or a KIAA0368 protein in the normal control is a positive indicator of said proliferative disease.

11. The method of item 6, wherein said fusion gene of KIAA0368-ROBO2 comprises a nucleic acid sequence, which is at least 70% identical to the sequence of SEQ ID NO: 2.

12. The method of item 10, wherein said fusion protein of KIAA0368-ROBO2 comprises an amino acid sequence, which is at least 70% identical to the sequence of SEQ ID NO: 1.

13. The method according to any of items 6 to 12, wherein said biological sample is selected from the group consisting of serum, plasma, urine, cerebrospinal fluid, cell extract, tissue, or a biopsy.

14. The method according to any one of items 6 to 13, wherein said proliferative disease is a glioma such as glioblastoma (GBM).

15. The method according to any one of items 10 to 14, wherein the amount of KIAA0368-ROBO2 is detected by immunoturbidimetric assay, immunofluorescence, immunodiffusion, enzyme-linked immunosorbent assay (ELISA), radioimmunoassay (RIA), Western blot, protein activity assay, Northern Blot, PCR, high performance liquid chromatography (HPLC), mass spectrometry (MS), gas chromatography (GC), GC-MS, LC-MS, or LC-MS/MS.

16. The method according to any one items 10 to 15, wherein the amount of KIAA0368-ROBO2 is detected on the basis of the protein level of a KIAA0368-ROBO2.

17. The method according to any one of items 10 to 16, wherein the amount of a KIAA0368-ROBO2 protein is detected using an antibody that specifically binds to said KIAA0368-ROBO2 protein.

18. The method according to any of items 10 to 16, wherein the amount of a KIAA0368-ROBO2 is detected by measuring the tyrosine kinase activity in said biological sample.

19. The method according to any one of items 10 to 15, wherein the amount of a KIAA0368-ROBO2 is detected on the basis of the mRNA level of said KIAA0368-ROBO2.

20. A method of diagnosing a proliferative disease, preferably a glioma such as glioblastoma in a subject, the method comprising:
   contacting biological sample from said subject with an antibody that binds to a KIAA0368-ROBO2 protein;
   allowing the antibody and the KIAA0368-ROBO2 protein to form an immune complex; and
   detecting the amount of immune complex formed as an indication of the amount of a KIAA0368-ROBO2 protein in said biological sample; and
   comparing the detected amount of a KIAA0368-ROBO2 protein to the amount of a KIAA0368-ROBO2 fusion protein and/or a ROBO2 protein and/or a KIAA0368 protein in a sample from normal control subject;
wherein a detected amount of a KIAA0368-ROBO2 protein that is elevated relative to the normal control is a positive indicator of said cancer.

21. The method according to any one of items 6 to 20, wherein said method is performed in vitro.

22. The method according to any one of items 6 to 21, wherein said biological sample and/or normal control sample has already been obtained from said subject and/or normal control subject prior to conducting said method.

23. Use of the nucleic acid according to any one of items 1 to 3, or the polypeptide according to any item 4 or 5 or the method according to any one items 6 to 22 for diagnosing and/or monitoring of tumor progression, preferably of the progression of brain tumors.

24. Use of the nucleic acid according to any one of items 1 to 3, or the polypeptide according to any item 4 or 5 or the method according to any one of items 6 to 22 for the subclassification of brain tumors and other proliferative diseases.

25. A recombinant polynucleotide molecule comprising the nucleic acid according to any one of items 1 to 3 plus expression-controlling elements operably linked with said nucleic acid to drive expression thereof.

26. An expression vector comprising the nucleic acid according to any one of items 1 to 3.

27. The expression vector encoding a polypeptide of item 4 or 5 operably linked to a promoter, said expression vector being present in a compatible host cell.

28. A mammalian, insect or bacterial host cell that has been genetically engineered by the insertion of a nucleic acid according to any one of items 1 to 3, which codes for a polypeptide of item 4 or 5.

29. A process for producing a polypeptide of item 4 or 5, which process comprises culturing the host cell of item 28 under conditions sufficient for the production of said protein.

30. The process of item 29 wherein said polypeptide is expressed at the surface of said cell and further includes the step of recovering the polypeptide or a fragment thereof from the culture.

31. An antibody that recognizes a polypeptide or a fragment thereof according to item 4 or 5 or as produced according to items 29 or 30.

32. The antibody of item 31, which recognizes a polypeptide having an amino acid sequence with at least 70% identity to the sequence of a fusion protein of KIAA0368-ROBO2 (SEQ ID NO: 1).

33. A method of screening for a compound capable of inhibiting the tyrosine kinase activity of at least one polypeptide of item 4 or 5, which method comprises incubating said polypeptide and a suitable substrate for said polypeptide in the presence of one or more test compounds or pharmaceutically acceptable salts thereof, measuring the tyrosine activity of said polypeptide, comparing said activity with comparable activity determined in the absence of a test compound, and selecting the test compound or compounds that reduce the tyrosine kinase activity of said polypeptide.

34. A tyrosine kinase inhibitor, which has been identified by the screening method of item 33.

35. The tyrosine kinase inhibitor of item 34, which is a small molecule inhibitor.

36. A tyrosine kinase inhibitor for use in the treatment of a proliferative disease, preferably glioma such as glioblastoma (GBM).

37. The antibody of item 31 or 32 for use in the treatment of proliferative disease, preferably glioma such as glioblastoma (GBM).

38. A small nucleotide such as a polynucleotide molecule having a sequence that is antisense to mRNA transcripts of the KIAA0368-ROBO2 fusion gene, for use in in the treatment of proliferative disease, preferably glioma such as glioblastoma (GBM).

39. The tyrosine kinase inhibitor for use according to item 36 and/or the antibody for use according to to item 37 and/or the small nucleotide for use according to item 38, wherein the treatment of said proliferative diseases is based on the on the presence of the KIAA0368-ROBO2 fustion gene and/or KIAA0368-ROBO2 fustion protein.

40. The antibody of item 31 or 32 for use in the method according to any one of items 10 to 22.

41. A pharmaceutical composition comprising a tyrosine kinase inhibitor, including pharmaceutically acceptable salts thereof, and/or an antibody of item 31 or 32.

42. A method of treating a proliferative disease, preferably glioma such as glioblastoma, comprising administering a therapeutically effective dose of a tyrosine kinase inhibitor and/or a small nucleotide such as a polynucleotide molecule having a sequence that is antisense to mRNA transcripts of the KIAA0368-ROBO2 fusion gene and/or an antibody of item 31 or 32 to a subject in need thereof.

43. The method according to item 40, wherein said method is based on the presence of the KIAA0368-ROBO2 fustion gene and/or KIAA0368-ROBO2 fustion protein.

44. Use of an antibody of item 31 or 32 for diagnosing a proliferative diseases, preferably glioma such as glioblastoma in a subject.

45. Use of an antibody of item 31 or 32 for diagnosing and/or monitoring of tumor progression, preferably of the progression of brain tumors.

46. Use of an antibody of item 31 or 32 for the subclassification of brain tumors and other proliferative diseases.

7. A kit for diagnosing a proliferative disease preferably glioma such as glioblastoma disease comprising an antibody that binds to a polypeptide of item 4 or 5 and an established standard of an amount of a KIAA0368-ROBO2 fusion protein and/or a ROBO2 protein and/or a KIAA0368 protein characteristic of a normal control subject.

48. Use of the kit of item 47 for diagnosing and/or monitoring of tumor progression, preferably of the progression of brain tumors.

49. Use of the kit of item 47 for the subclassification of brain tumors and other proliferative diseases.

50. A method for determining whether a subject suffering from a proliferative disease is susceptible to treatment with a tyrosine kinase inhibitor, comprising detecting the expression of a KIAA0368-ROBO2 fusion protein in biological sample of said subject, wherein an elevated amount of a KIAA0368-ROBO2 fusion protein indicates that said subject is susceptible to treatment with a tyrosine kinase inhibitor.

In accordance with a preferred aspect of the present invention, there is provided a nucleic acid sequence (polynucleotide) of SEQ ID NO: 2 of a novel fusion gene KIAA0368-ROBO2.

In a further preferred aspect of the present invention, the KIAA0368-ROBO2 fusion gene comprises one or more nucleotide sequences of a fragment of a gene, said fragment having a sequence selected from the KIAA0368 gene (SEQ ID NO 3) and ROBO2 gene (SEQ ID NO 4).

According to the present invention, the fusion gene results from an unbalanced translocation between human chromosomes 3 and 9 (see Focus 1 in FIG. 1). Using array comparative genome hybridization (aCGH), a method that can detect genomic gains and losses of more than 10 kb, the breakpoints could be detected, wherein said breakpoints are located within the genes ROBO2 and KIAA0368 on chromosomes 3 and 9 respectively (see FIG. 2). More specifically, the latter parts of ROBO2 are under the control of the promoter of KIAA0368. Moreover, within the fusion protein, a valine residue is created from a codon formed from parts of KIAA0368 and Robo2 (see capital non-bold letter V in FIG. 5).

A "genomic translocation/rearrangement" is a structural variation resulting of a change in position of a chromosomal segment within a genome. Translocations can happen within the same chromosome (intra-chromosomal) or between two different chromosomes (inter-chromosomal). The rearrangement sometimes causes the fusion of one or more genes (fusion gene). This fusion then results in a misal location and may cause altered expression, and/or total or partial disruption of one or more of the genes comprised in said fusion gene. The rearrangement that fuses two genes resulting in the production of an active protein is called "activating fusion gene". Hence, an activating fusion gene codes for a "fusion protein" with a new or altered activity. In contrast, a rearrangement may also produce fusion gene that does not code for a functional protein but leads to a loss of function of one or more genes involved. Such fusion gene is also referred to herein as "inactivating fusion gene".

In addition a fusion gene may also be the result of a trans-splicing event. Hence, this fusion is not the result of a genomic event but a transcriptional mechanism. Whilst genomic rearrangements can be observed by cytogenetic techniques on affected cells, trans-splicing can only be detected by transcriptome sequencing.

The term "fusion gene" as used herein includes activating fusion genes, inactivating fusion genes and trans-spliced genes, e.g. regulatory fusion genes.

Hence, a "fusion gene" as used herein refers to a hybrid gene (or transcript) formed from two previously separate genes or fragments thereof and thus resulting in gene rearrangement so that the previously separate genes or fragments thereof are transcribed in, or present on a single transcript. Alternatively, the separate genes may undergo rearrangement independently before they fuse to each other.

Accordingly "fused gene" may be construed accordingly to refer to any such rearrangement event. Fused genes can occur as the result of mutations such as translocation (intrachromosomal rearrangements or inter-chromosomal rearrangements), deletion, inversion, amplification and/or insertion. Moreover fusion genes may also occur as a result of post-transcriptional rearrangements or modifications, like trans-splicing or the like. The resulting fusion gene causes a misallocation, and/or altered expression, and/or total or partial disruption of one or more of the genes comprised in said fusion gene. A fusion gene according to the present invention comprises one or more nucleotide sequences encoding a protein or a fragment of the protein.

"Translocation" of genes results in a chromosome abnormality caused by rearrangement of parts between non-homologous chromosomes or between regions within the same chromosome. It is detected on cytogenetics or a karyotype of affected cells. "Deletions" in chromosomes may be of one or more entire genes or only a portion of one or more genes. Genetic "insertion" is the addition of one or more nucleotide base pairs into a genetic sequence.

The polynucleotides of the present invention may be in the form of RNA or in the form of DNA; DNA should be understood to include cDNA, genomic DNA, and synthetic DNA. The DNA may be double-stranded or single-stranded and, if single stranded, may be the coding strand or non-coding (antisense) strand. The coding sequence, which encodes the polypeptide may be identical to the coding sequence shown in SEQ ID NOS 2 to 4, or it may be a different coding sequence encoding the same polypeptide, as a result of the redundancy or degeneracy of the genetic code or a single nucleotide polymorphism. For example, it may also be an RNA transcript which includes the entire length of any one of SEQ ID NOS 2 to 4.

The polynucleotides which encode the polypeptide of SEQ ID NO: 1 may include but are not limited to the coding sequence for the polypeptide alone; the coding sequence for the polypeptide plus additional coding sequence, such as a leader or secretory sequence or a proprotein sequence; and the coding sequence for the polypeptide (and optionally additional coding sequence) plus non-coding sequence, such as introns or a non-coding sequence 5' and/or 3' of the coding sequence for the polypeptide.

Thus, the term "polynucleotide encoding a polypeptide" or the term "nucleic acid encoding a polypeptide" should be understood to encompass a polynucleotide or nucleic acid which includes only coding sequence for a KIAA0368-ROBO2 fusion protein, e.g. the polypeptide of SEQ ID NO 1 as well as one which includes additional coding and/or non-coding sequence. The terms polynucleotides and nucleic acid are used interchangeably.

The present invention also includes polynucleotides where the coding sequence for the polypeptide may be fused in the same reading frame to a polynucleotide sequence which aids in expression and secretion of a polypeptide from a host cell; for example, a leader sequence which functions as a secretory sequence for controlling transport of a polypeptide from the cell may be so fused. The polypeptide having such a leader sequence is termed a preprotein or a preproprotein and may have the leader sequence cleaved, by the host cell to form the mature form of the protein. These polynucleotides may have a 5' extended region so that it encodes a proprotein, which is the mature protein plus additional amino acid residues at the N-terminus. The expression product having such a prosequence is termed a proprotein, which is an inactive form of the mature protein; however, once the prosequence is cleaved an active mature protein remains. Thus, for example, the polynucleotides of the present invention may encode polypeptides, or proteins having a prosequence, or proteins having both a prosequence and a presequence (leader sequence).

The polynucleotides of the present invention may also have the coding sequence fused in frame to a marker sequence which allows for purification of the polypeptides of the present invention. The marker sequence may be a polyhistidine tag, a hemagglutinin (HA) tag, a c-myc tag or a V5 tag when a mammalian host, e. g. COS-1 cells, is used.

The HA tag would correspond to an epitope derived from the influenza hemagglutinin protein (Wilson, I., et al., Cell, 37: 767 (1984)), and the c-myc tag may be an epitope from human Myc protein (Evans, G. I. et al., Mol. Cell. Bio. 5: 3610-3616(1985)).

The term "gene" means the segment of DNA involved in producing a polypeptide chain; it includes regions preceding and following the coding region (leader and trailer) as well as intervening sequences (introns) between individual coding segments (exons).

Fragments of the full-length genes of the present invention may be used as a hybridization probe for a cDNA library to isolate full-length cDNA as well as to isolate other cDNAs, which have significant sequence homology to the gene and will encode proteins or polypeptides having similar biological activity or function. Such a probe of this type has at least 14 bases (at least 14 contiguous nucleotides from one of SEQ ID NOS: 2 to 4), preferably at least 30 bases, and such may contain, for example, 50 or more bases. Preferred are the probes of SEQ ID NOS 5 to 8. Such probe may also be used to identify a cDNA clone corresponding to a full-length transcript and/or a genomic clone or clones that contain the complete gene, including regulatory and promoter regions, exons, and introns. Labelled oligonucleotides having a sequence complementary to that of the gene of the present invention are useful to screen a library of human cDNA, genomic DNA or mRNA or similar libraries from other sources or animals to locate members of the library to which the probe hybridizes. As an example, a known DNA sequence may be used to synthesize an oligonucleotide probe, which is then used in screening a library to isolate the coding region of a gene of interest.

The present invention is considered to further provide polynucleotides which hybridize to the hereinabove-described sequences wherein there is at least 70%, preferably at least 90%, and more preferably at least 95% identity or similarity between the sequences, and thus encode proteins having similar biological activity. Moreover, as known in the art, there is "similarity" between two polypeptides when the amino acid sequences contain the same or conserved amino acid substitutes for each individual residue in the sequence. Identity and similarity may be measured using sequence analysis software (e.g., ClustalW at PBIL (Pôle Bioinformatique Lyonnais) http://npsa-pbil.ibcp.fr). The present invention particularly provides such polynucleotides, which hybridize under stringent conditions to the hereinabove-described polynucleotides. As herein used, the term "stringent conditions" means conditions which permit hybridization between polynucleotides sequences and the polynucleotide sequences of SEQ ID NOS: 2 to 4 where there is at least about 70% identity.

Suitably stringent conditions can be defined by, e.g., the concentrations of salt or formamide in the prehybridization and hybridization solutions, or by the hybridization temperature, and are well known in the art. In particular, stringency can be increased by reducing the concentration of salt, by increasing the concentration of formamide, and/or by raising the hybridization temperature.

For example, hybridization under high stringency conditions may employ about 50% formamide at about 37° C. to 42° C., whereas hybridization under reduced stringency conditions might employ about 35% to 25% formamide at about 30° C. to 35° C. One particular set of conditions for hybridization under high stringency conditions employs 42° C., 50% formamide, 5x. SSPE, 0.3% SDS, and 200 µg/ml sheared and denatured salmon sperm DNA. For hybridization under reduced stringency, similar conditions as described above may be used in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art. Preferably, hybridization should occur only if there is at least 95%, and more preferably at least 97%, identity between the sequences. The polynucleotides which hybridize to the hereinabove described polynucleotides in a preferred embodiment encode polypeptides which exhibit substantially the same biological function or activity as the mature protein encoded by one of the cDNAs of SEQ ID NOS: 2 to 4.

As mentioned, a suitable polynucleotide probe may have at least 14 bases, preferably 30 bases, and more preferably at least 50 bases, and will hybridize to a polynucleotide of the present invention, which has an identity thereto, as hereinabove described, and which may or may not retain activity. For example, such polynucleotides may be employed as a probe for hybridizing to the polynucleotides of SEQ ID NOS: 2 to 4 respectively, for example, for recovery of such a polynucleotide, or as a diagnostic probe, or as a PCR primer. Thus, the present invention includes polynucleotides having at least a 70% identity, preferably at least a 90% identity, and more preferably at least a 95% identity to a polynucleotide which encodes the polypeptide of SEQ ID NOS 1, as well as fragments thereof, which fragments preferably have at least 30 bases and more preferably at least 50 bases, and to polypeptides encoded by such polynucleotides.

The terms "homology" or "identity," as used interchangeably herein, refer to sequence similarity between two polynucleotide sequences or between two polypeptide sequences, with identity being a more strict comparison. The phrases "percent identity or homology" and "identity or homology" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that can be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences. The term "substantially identical," as used herein, refers to an identity or homology of at least 70%, 75%, at least 80%, at least 85%, at least 90%, 91%, 92%, 93%, 94%, 95%, 96%, 97%, 98%, 99%, or more.

As is well known in the art, the genetic code is redundant in that certain amino acids are coded for by more than one nucleotide triplet (codon), and the invention includes those polynucleotide sequences which encode the same amino acids using a different codon from that specifically exemplified in the sequences herein. Such a polynucleotide sequence is referred to herein as an "equivalent" polynucleotide sequence. The present invention further includes variants of the hereinabove described polynucleotides which encode for fragments, such as part or all of the protein, analogs and derivatives of the polypeptide of SEQ ID NOS 1. The variant forms of the polynucleotide may be a naturally occurring allelic variant of the polynucleotide or a non-naturally occurring variant of the polynucleotide. For example, the variant in the nucleic acid may simply be a difference in codon sequence for the amino acid resulting from the degeneracy of the genetic code, or there may be deletion variants, substitution variants and addition or insertion variants. As known in the art, an allelic variant is an alternative form of a polynucleotide sequence, which may have a substitution, deletion or addition of one or more nucleotides that does not substantially alter the biological function of the encoded polypeptide.

The present invention further includes polypeptides, which have the deduced amino acid sequence of SEQ ID NO 1, as well as fragments, analogs and derivatives of such polypeptides. The terms "fragment", "derivative" and "analog", when referring to the polypeptide of SEQ ID NO 1, means polypeptides that retain essentially the same biological function or activity as such polypeptides. An analog might, for example, include a proprotein, which can be activated by cleavage of the proprotein portion to produce an active mature protein. The polypeptides of the present invention may be recombinant polypeptides, natural polypeptides or synthetic polypeptide.

The fragment, derivative or analog of a polypeptide of SEQ ID NO 1, may be (i) one in which one or more of the amino acid residues is substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which additional amino acids are fused to the mature protein, such as a leader or secretory sequence or a sequence which is employed for purification of the mature polypeptide or a proprotein sequence. Such fragments, derivatives and analogs are deemed to be within the scope of those skilled in the art to provide upon the basis of the teachings herein.

The polypeptides and polynucleotides of the present invention should be in an isolated form, and preferably they are purified to substantial homogeneity or purity. By substantial homogeneity is meant a purity of at least about 85%.

The term "isolated" is used to mean that the material has been removed from its original environment (e. g., the natural environment if it is naturally occurring). For example, a naturally occurring polynucleotide or polypeptide present in a living animal is not considered to be isolated, but the same polynucleotide or polypeptide, when separated from substantially all of the coexisting materials in the natural system, is considered isolated. For DNA, the term includes, for example, a recombinant DNA which is incorporated into a vector, into an autonomously replicating plasmid or virus, or into the genomic DNA of a prokaryote or eukaryote; or which exists as a separate molecule (e. g., a cDNA or a genomic or cDNA fragment produced by polymerase chain reaction (PCR) or restriction endonuclease digestion) independent of other sequences. It also includes a recombinant DNA, which is part of a hybrid gene encoding additional polypeptide sequence, e.g., a fusion protein. Further included is recombinant DNA which includes a portion of the nucleotides shown in one of SEQ ID NOS 2 to 4.

The polypeptides of the present invention include the polypeptide of SEQ ID NOS 1, as well as polypeptides which have at least 75% similarity (e. g. preferably at least 50%; and more preferably at least 70% identity) to the polypeptide of SEQ ID NOS 1, more preferably at least 85% similarity (e. g. preferably at least 70% identity) to the polypeptide of SEQ ID NOS 1, and most preferably at least 95% similarity (e. g. preferably at least 90% identity) to the polypeptide of SEQ ID NOS 1. Moreover, they should preferably include exact portions of such polypeptides containing a sequence of at least 30 amino acids, and more preferably at least 50 amino acids.

Fragments or portions of the polypeptides of the present invention may be employed as intermediates for producing the corresponding full-length polypeptides by peptide synthesis. Fragments or portions of the polynucleotides of the present invention may also be used to synthesize full-length polynucleotides of the present invention.

The present invention also includes vectors, which include such polynucleotides, host cells which are genetically engineered with such vectors and the production of polypeptides by recombinant techniques using the foregoing. Host cells are genetically engineered (transduced or transformed or transfected) with such vectors, which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those commonly used with the host cell selected for expression, as well known to the ordinarily skilled artisan.

The polynucleotides of the present invention may be employed for producing polypeptides by recombinant techniques. Thus, for example, the polynucleotides may be included in any one of a variety of expression vectors for expressing polypeptides. Such vectors include chromosomal, nonchromosomal and synthetic DNA sequences, e. g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by any of a variety of procedures. In general, the DNA sequence is inserted into an appropriate restriction endonuclease site(s) by procedures well known in the art, which procedures are deemed to be within the scope of those skilled in this art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli* lac or trp, the phage lambda P.sub.L promoter and other promoters known to control expression of genes in prokaryotic or eukaryotic cells or their viruses.

The expression vector should also contain a ribosome binding site for translation initiation and a transcription terminator. The vector may also include appropriate sequences for amplifying expression. In addition, the expression vectors preferably contain one or more selectable marker genes to provide a phenotypic trait for selection of transformed host cells, such as dihydrofolate reductase or neomycin-resistance for eukaryotic cell culture, or such as tetracycline- or ampicillin-resistance in *E. coli*.

The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as *E. coli, Streptomyces, Salmonella typhimurium*; fungal cells, such as yeast; insect cells, such as *Drosophila* S2 and *Spodoptera* Sf9; animal cells, such as CHO, COS or Bowes melanoma; adenoviruses; plant cells, etc. The selection of an appropriate host is deemed to be within the scope of those skilled in the art from the teachings herein.

Synthetic production of nucleic acid sequences is well known in the art as is apparent from CLONTECH 95/96 Catalogue, pages 215-216, CLONTECH, 1020 East Meadow Circle, Palo Alto, Calif. 94303. Thus, the present invention also includes expression vectors useful for the production of the proteins of the present invention. The present invention further includes recombinant constructs comprising one or more of the sequences as broadly described above. The constructs may comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example: Bacterial: pQE70, pQE60, pQE-9 (Qiagen), pBS, pD10, phagescript, psiX174, pbluescript SK, pbsks, pNH8A, pNH16a, pNHI8A, pNH46A (Stratagene), ptrc99a, pKK223-3, pKK233-3, pDR540 and pRIT5 (Pharmacia); and Eukaryotic: pWLNEO, pSV2CAT, pOG44, pXTI, pSG (Stratagene), pSVK3, pBPV, pMSG, and pSVL (Pharmacia). However, any other suitable plasmid or vector may be used as long as it is replicable and viable in the host.

Promoter regions can be selected from any desired gene using CAT (chloramphenicol acetyl transferase) vectors or other vectors with selectable markers.

Two appropriate vectors are pKK232-8 and pCM7. Particular named bacterial promoters include lacI, lacZ, T3, T7, gpt, lambda P.sub.R, P.sub.L and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

Components of the expression vector may generally include: 1) a neomycin phosphotransferase (G418), or hygromycin B phosphotransferase (hyg) gene as a selection marker, 2) an *E. coli* origin of replication, 3) a T7 and SP6 phage promoter sequence, 4) lac operator sequences, 5) the lactose operon repressor gene (lacIq) and 6) a multiple cloning site linker region. Such an origin of replication (oriC) may be derived from pUC19 (LTI, Gaithersburg, Md.).

In a further embodiment, the present invention provides host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, lipofection or electroporation (Davis, L., Dibner, M., Battey, I., Basic Methods in Molecular Biology, (1986)).

Such constructs in host cells are preferably used in a conventional manner to produce the gene product encoded by the recombinant sequence. Alternatively, the polypeptides of the invention can be synthetically produced by conventional peptide synthesizers or by chemical ligation of suitable fragments thus prepared.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

Transcription of the DNA encoding the polypeptides of the present invention by higher eukaryotes is increased by inserting an enhancer sequence into the vector.

Enhancers include cis-acting elements of DNA, usually about from 10 to 300 bp, that act on a promoter to increase its transcription. Examples include the SV40 enhancer on the late side of the replication origin bp 100 to 270, acytomegalovirus early promoter enhancer, the polyoma enhancer on the late side of the replication origin, and adenovirus enhancers.

Generally, recombinant expression vectors will include origins of replication and selectable markers permitting transformation of the host cell, e. g., the ampicillin resistance gene of E. coli and S. cerevisiae TRP1 gene, and a promoter derived from a highly expressed gene to direct transcription of a downstream structural sequence. Such promoters can be derived from operons encoding glycolytic enzymes, such as 3-phosphoglycerate kinase (PGK), alpha-factor, acid phosphatase, or heat shock proteins, among others.

The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter.

The vector will comprise one or more phenotypic selectable markers and an origin of replication to ensure maintenance of the vector and to, if desired, provide amplification within the host. Suitable prokaryotic hosts for transformation include E. coli, Bacillus subtilis, Salmonella typhimurium and various species within the genera Pseudomonas, Streptomyces and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, the selected promoter is induced by appropriate means (e. g., temperature shift or chemical induction), and cells are cultured for an additional period.

Cells are typically harvested by centrifugation and then disrupted by physical or chemical means, with the resulting crude extract being retained for further purification.

Microbial cells employed in expression of proteins can be disrupted by any convenient method, including freeze-thaw cycling, sonication, mechanical disruption and use of cell-lysing agents; such methods are well known to those skilled in the art.

Various mammalian cell culture systems can also be employed to express a recombinant protein. Examples of mammalian expression systems include the COS-7 lines of monkey kidney fibroblasts, described by Gluzman, Cell, 23: 175 (1981). Other cell lines capable of expressing a compatible vector include, for example, the C127, 3T3, CHO, HeLa and BHK cell lines. Mammalian expression vectors will generally comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Recovery can be facilitated if the polypeptide is expressed at the surface of the cells, but such is not a prerequisite. Recovery may also be desirable of cleavage products that are cleaved following expression of a longer form of the polypeptide. Protein refolding steps as known in this art can be used, as necessary, to complete configuration of the mature protein. High performance liquid chromatography (HPLC) can be employed for final purification steps.

The polypeptides of the present invention may be purified natural products, or produced by recombinant techniques from a prokaryotic or eukaryotic host (for example, by bacterial, yeast, higher plant, insect or mammalian cells in culture). Depending upon the host employed in a recombinant production procedure, the polypeptides of the present invention may be glycosylated or may be non-glycosylated. Polypeptides of the invention may also include an initial methionine amino acid residue.

In a preferred embodiment, the proteins of the invention are isolated and purified so as to be substantially free of contamination from other proteins. For example, the proteins of the invention should constitute at least 80% by weight of the total protein present in a sample, more preferably at least 90%, even more preferably at least 95%, and most preferably at least 98% by weight of the total protein.

These proteins may be in the form of a solution in water, another suitable solvent, such as dimethyl sulphoxide (DMSO) or ethanol, or a mixture of suitable solvents.

Examples of mixtures of solvents include 10% (by weight) ethanol in water and 2% (by weight) DMSO in water. A solution may further comprise salts, buffering agents, chaotropic agents, detergents, preservatives and the like. Alternatively, the proteins may be in the form of a solid, such as a lyophilized powder or a crystalline solid, which may also comprise a residual solvent, a salt or the like.

The invention further relates to antibodies, which bind to the KIA0368-ROBO2 fusion protein of the invention.

As used herein, the term "antibodies" includes polyclonal antibodies, affinity-purified polyclonal antibodies, monoclonal antibodies, and antigen-binding fragments, such as F(ab')2 and Fab' proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans should be reduced.

Alternative techniques for generating or selecting antibodies useful herein include in vitro exposure of lymphocytes to a KIAA0368-ROBO2 fusion protein, e.g. the polypeptide of SEQ ID NO 1 or a fragment or peptide therefrom, and selection of antibody display libraries in phage or similar vectors (for instance, through use of immobilized or labeled KIAA0368-ROBO2 fusion protein, e.g. polypeptide of SEQ ID NO 1 or peptide therefrom).

As would be evident to one of ordinary skill in the art, polyclonal antibodies can be generated from inoculating a variety of warm-blooded animals, such as horses, cows, goats, sheep, dogs, chickens, rabbits, mice and rats, with a KIAA0368-ROBO2 fusion protein, e.g. a polypeptide of SEQ ID NO 1 or a fragment thereof. The immunogenicity of a KIAA0368-ROBO2 fusion protein may be increased through the use of an adjuvant, such as alum (aluminum hydroxide) or Freund's complete or incomplete adjuvant, or surface active substances, such as lysolecithin, pluronic polyols, polyanions, peptides, oil emulsions, KLH or dinitrophenol. Among adjuvants used in humans, BCG (bacilli Calmette-Guerin) and *Corynebacterium parvum* are especially preferable. Polypeptides useful for immunization also include fusion polypeptides, such as fusions of a KIAA0368-ROBO2 fusion protein, e.g. a polypeptide of SEQ ID NO 1 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier, such as keyhole limpet hemocyanin (KLH), bovine serum albumin (BSA) or tetanus toxoid, for immunization. Antibodies to the KIAA0368-ROBO2 fusion protein may also be generated using methods that are well known in the art. Such antibodies may include, but are not limited to, polyclonal, monoclonal, chimeric, and single chain antibodies, Fab fragments, and fragments produced by a Fab expression library.

Neutralizing antibodies (i.e., those which block or modify interactions at the active sites) are especially preferred herein for therapeutic use.

For the production of antibodies, binding proteins, or peptides which bind specifically to the polypeptide of SEQ ID NO 1, libraries of single chain antibodies, Fab fragments, other antibody fragments, non-antibody protein domains, or peptides may be screened. The libraries could be generated using phage display, other recombinant DNA methods, or peptide synthesis (Vaughan, T. J. et al. Nature Biotechnology 14: 309-314 (1966)). Such libraries would commonly be screened using methods, which are well known in the art to identify sequences which demonstrate specific binding to the polypeptide of SEQ ID NO 1.

It is preferred that the oligopeptides, peptides, or fragments used to induce antibodies to the KIAA0368-ROBO2 fusion protein have an amino acid sequence consisting of at least about 5 amino acids, and more preferably, of at least about 10 amino acids. It is also preferable that these oligopeptides, peptides, or fragments are identical to a portion of the amino acid sequence of the natural protein. Short stretches of amino acids of the KIAA0368-ROBO2 fusion protein may also be fused with those of another protein, such as KLH, and antibodies to the chimeric molecule may be produced.

Monoclonal antibodies to the KIAA0368-ROBO2 fusion protein may be prepared using any well known technique which provides for the production of antibody molecules by continuous cell lines in culture. These include, but are not limited to, the hybridoma technique, the human B-cell hybridoma technique, and the EBV-hybridoma technique, although monoclonal antibodies produced by hybridoma cells may be preferred.

In addition, techniques developed for the production of "chimeric antibodies", such as the splicing of mouse antibody genes to human antibody genes to obtain a molecule with appropriate antigen specificity and biological activity, can be used, see Neuberger, M. S. et al. Nature 312: 604-608 (1984). Alternatively, techniques described for the production of single chain antibodies may be adapted, using methods known in the art, to produce single chain antibodies with specificity for the polypeptide of SEQ ID NO 1. Antibodies with related specificity, but of distinct idiotypic composition, may be generated by chain shuffling from random combinatorial immunoglobulin libraries. (Burton D. R. Proc. Natl. Acad. Sci. 88: 11120-11123 (1991)).

Antibodies may also be produced by inducing in vivo production in the lymphocyte population or by screening immunoglobulin libraries or panels of highly specific binding reagents as disclosed in the literature. (Orlandi, R. et al. Proc. Natl. Acad. Sci. 86: 3833-3837 (1989)).

Antibody fragments, which contain specific binding sites for the KIAA0368-ROBO2 fusion protein may also be generated. For example, such fragments include, but are not limited to, $F(ab')_2$ fragments produced by pepsin digestion of the antibody molecule and Fab fragments generated by reducing the disulfide bridges of the $F(ab')_2$ fragments. Alternatively, Fab expression libraries may be constructed to allow rapid and easy identification of monoclonal Fab fragments with the desired specificity. (Huse, W. D. et al. Science 254: 1275-1281(1989)).

Various immunoassays may be used to identify antibodies having the desired specificity. Numerous protocols for competitive binding or immunoradiometric assays using either polyclonal or monoclonal antibodies with established specificities are well known in the art. Such immunoassays typically involve the measurement of complex formation between the KIAA0368-ROBO2 fusion protein and its specific antibody. A two-site, monoclonal-based immunoassay utilizing monoclonal antibodies reactive to two non-interfering epitopes of the KIAA0368-ROBO2 fusion protein is preferred, but a competitive binding assay may also be employed.

As earlier mentioned, the KIAA0368-ROBO2 fusion protein can be used in treatment of diseases, in particular proliferative diseases, such as glioma such as glioblastoma.

Pharmaceutical compositions suitable for use in this aspect of the invention include compositions wherein the active ingredients are contained in an effective amount to achieve the intended purpose relating to one of the diseases. The determination of a therapeutically effective dose is well within the capability of those skilled in the art and can be estimated initially either in cell culture assays, e. g. of neoplastic cells, or in animal models, usually mice, rats, rabbits, dogs, or pigs. An animal model may also be used to determine the appropriate concentration range and route of administration, which information is then commonly used to determine useful doses and routes for administration in humans.

A therapeutically effective dose refers to that amount of active ingredient, e.g. an antibody of the KIAA0368-ROBO2 fusion protein, or an agonist, antagonist or inhibitor of the KIAA0368-ROBO2 fusion protein, which ameliorates particular symptoms or conditions of the disease. For example, the amount to be administered may be effective to inhibit the tyrosine kinase activity of the KIAA0368-ROBO2 fusion protein. Therapeutic efficacy and toxicity may likewise be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of toxic to therapeutic effects is the therapeutic index, and it can be expressed as the LD50/ED50 ratio. Pharmaceutical compositions, which exhibit large therapeutic indices, are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, the sensitivity of the patient, and the route of administration.

An exact dosage will normally be determined by the medical practitioner in light of factors related to the subject requiring treatment, with dosage and administration being adjusted to provide a sufficient level of the active moiety or to maintain a desired effect. Factors to be taken into account include the severity of the disease state, the general health of the subject, the age, weight, and gender of the subject, diet, time and frequency of administration, drug combination(s), reaction sensitivities, and tolerance/response to therapy. Long-acting pharmaceutical compositions may be administered every 3 to 4 days, every week, or even once every two weeks, depending on the half-life and clearance rate of the particular formulation.

Yet another aspect of the invention provides polynucleotide molecules having sequences that are antisense to mRNA transcripts of a polynucleotide of SEQ ID NOS 2 to 4. Administration of an antisense polynucleotide molecule can block the production of the protein encoded by the polynucleotides of SEQ ID NOS 2 to 4. The techniques for preparing antisense polynucleotide molecules and administering such molecules are known in the art. For example, antisense polynucleotide molecules can be encapsulated into liposomes for fusion with cells.

In particular, the expression of the polynucleotides of SEQ ID NOS 2 to 4 in brain, prostate, lung, heart, liver, spleen and kidney tissue, most preferably in brain, provides evidence for a potential role in the pathophysiology of the diseases described above. Therefore, in a further aspect, the invention relates to diagnostic assays for detecting diseases associated with inappropriate activity or expression levels of the KIAA0368-ROBO2 fusion protein. Antibodies that specifically bind to the KIAA0368-ROBO2 fusion protein may be used for the diagnosis of disorders characterized by expression of the KIAA0368-ROBO2 fusion protein, or in assays to monitor patients being treated with agonists or antagonists (inhibitors) of the KIAA0368-ROBO2 fusion protein. Antibodies useful for diagnostic purposes may be prepared in the same manner as those described above for therapeutics. Diagnostic assays for the KIAA0368-ROBO2 fusion protein include methods that utilize the antibody and a label to detect the KIAA0368-ROBO2 fusion protein in human body fluids or in extracts of cells or tissues. The antibodies may be used with or without modification, and they may be labeled by covalent or non-covalent joining with a reporter molecule. A wide variety of reporter molecules are known in the art. Recombinant KIAA0368-ROBO2 fusion proteins that have been modified so as to be catalytically inactive can also be used as dominant negative inhibitors. Such modifications include, for example, mutation of the active site.

A variety of protocols for measuring the KIAA0368-ROBO2 fusion protein, including ELISAs, RIAs and FACS, are known in the art and provide a basis for diagnosing altered or abnormal levels of the expression of the KIAA0368-ROBO2 fusion protein. Normal or standard values for the expression of ROBO2 and/or KIAA0368 are established by combining body fluids or cell extracts taken from normal mammalian subjects, preferably human, with an antibody to the ROBO2 and/or KIAA0368 under conditions suitable for complex formation. The method for detecting the KIAA0368-ROBO2 fusion protein in a biological sample would comprise the steps of a) providing a biological sample; b) combining the biological sample and an anti-KIAA0368-ROBO2 antibody under conditions which are suitable for complex formation to occur between KIAA0368-ROBO2 and the antibody; and c) detecting complex formation between the KIAA0368-ROBO2 fusion protein and the antibody, thereby establishing the presence of the KIAA0368-ROBO2 fusion protein in the biological sample.

The amount of complex formation then may be quantified by various methods, preferably by photometric means. Quantities of the KIAA0368-ROBO2 fusion protein expressed in a subject, control, and disease samples from biopsied tissues are compared with the standard values. Deviation between standard and subject values establishes the parameters for diagnosing disease.

In another embodiment of the invention, the polynucleotides encoding the KIAA0368-ROBO2 fusion gene and fragments thereof are used for diagnostic purposes, which polynucleotides may include oligonucleotide sequences, complementary RNA and DNA molecules, and PNAs. These polynucleotides may be used to detect and quantitate gene expression in biopsied tissues in which expression of the KIAA0368-ROBO2 fusion genes may be correlated with one of the diseases. The diagnostic assay may be used to distinguish between absence, presence, and excess expression of the KIAA0368-ROBO2 fusion gene and/or fusion protein and to monitor regulation of the levels of the KIAA0368-ROBO2 fusion protein during therapeutic intervention.

KIAA0368-ROBO2 polynucleotide and polypeptide sequences, fragments thereof, antibodies of KIAA0368-ROBO2, and agonists, antagonists or inhibitors of KIAA0368-ROBO2 can be used as discovery tools to identify molecular recognition events and therefore proteins, polypeptides and peptides that interact with the KIAA0368-ROBO2 fusion proteins. A specific example is phage display peptide libraries where greater than $10^8$ peptide sequences can be screened in a single round of panning Such methods as well as others are known within the art and can be utilized to identify compounds that inhibit or enhance the activity of a KIAA0368-ROBO2 fusion protein.

Coupled links represent functional interactions such as complexes or pathways, and proteins that interact with a KIAA0368-ROBO2 fusion protein can be identified by a yeast two-hybrid system, proteomics (differential 2D gel analysis and mass spectrometry) and genomics (differential gene expression by microarray or serial analysis of gene expression SAGE).

Proteins identified as functionally linked to the KIAA0368-ROBO2 fusion protein and the process of interaction form the basis of methods of screening for inhibitors, agonists and antagonists and modulators of these interactions of the KIAA0368-ROBO2 fusion protein.

The term "antagonist", as it is used herein, refers to an inhibitor molecule which, when bound to a KIAA0368-ROBO2 fusion protein, decreases the amount or the duration of the effect of the biological or immunological activity of said KIAA0368-ROBO2 fusion protein, e. g. decreasing the enzymatic activity, e.g. the tyrosine kinase activity. Antagonists may include proteins, nucleic acids, carbohydrates, antibodies, or any other molecules which decrease the effect of a KIAA0368-ROBO2 fusion protein; for example, they may include small molecules and organic compounds that bind to and inactivate a KIAA0368-ROBO2 fusion protein by a competitive or non-competitive type mechanism. Preferred are small molecule inhibitors of a KIAA0368-ROBO2 fusion protein. Most preferred are competitive small molecule inhibitors of said KIAA0368-ROBO2 fusion protein.

It has been shown that the KIAA0368-ROBO2 fusion protein has the enzymatic activity of tyrosine kinase.

Accordingly, inhibitors can be inhibitors of tyrosine kinase. The term "tyrosine kinase inhibitor" is generally known to a person skilled in the art and means enzyme inhibitors, which inhibit the catalytic activity of a tyrosine kinase, preferably by direct interaction of the inhibitor with the enzyme.

The term "tyrosine kinase inhibitor" defines in the context of the present invention a compound or a plurality of compounds which interact(s) with tyrosine kinase (preferably the human ROBO2) such that the kinase activity is reduced. Assays which are suitable to detect such inhibitors are explained in more detail herein below. The term "plurality of compounds" is to be understood as a plurality of substances which may or may not be identical. The plurality of compounds may preferably act additively or synergistically. Said compound or plurality of compounds may be chemically synthesized or microbiologically produced and/ or comprised in, for example, samples, e.g., cell extracts from, e.g., plants, animals or microorganisms.

The term "reduced tyrosine kinase activity" or "reducing the tyrosine kinase activity" as used herein defines the reduction of the kinase activity of ROBO2, preferably to at least about the same level as compared to a normal/natural state of a comparable control subject. In this context, the term "normal/natural state of a comparable control subject" means the tyrosine kinase activity of ROBO2 in a control sample which is preferably of the same nature as the test sample (e.g. both cells are epithelial cells) but which is derived from a different source. "A different source" includes e.g. a tissue sample obtained from a healthy subject, preferably from a subject who does not suffer from a proliferative disease or a tissue sample obtained from a distinct part of the same subject wherein said distinct part appears to be free from associated symptoms of said proliferative disease. However, even in cases where the inhibitor of ROBO2 will not reduce the kinase activity of ROBO2 to about the normal/natural state of a comparable control subject but actually reduces the ROBO2 kinase activity when compared to the ROBO2 kinase activity before the addition of said inhibitor, it will be appreciated that said inhibitor has a beneficial effect.

Accordingly, it is envisaged that an inhibitor of the tyrosine kinase activity of ROBO2 at least reduces the kinase activity of ROBO2 about 5%, 10%, 20%, 30%, 40%, 50%, 60%, 70%, 80%, 90% or even 100% when compared to the ROBO2 kinase activity that is achieved without the addition of said inhibitor. Suitable test systems to measure the ROBO2 kinase activity are disclosed herein. Accordingly, it is preferred that the inhibitors of the present invention reduce the kinase activity of ROBO2 about 5%, 10%, 20%, 30%, 40%, 50%, 60%, 70%, 80%, 90% or even 100%, for example under conditions which are similar or identical to the test system disclosed herein (for example the ROBO2 enzyme test).

In light of the correlation with tyrosine kinase inhibition, in preferred embodiments, the subject method and medical use utilize an agent, if such determination is applicable, with a $K_i$ for tyrosine kinase inhibition of 10 μM or less, more preferably of 1 μM or less, even more preferably of 0.1 μM or less or 0.01 μM or less, or most preferably 0.01 μM or less. Indeed, inhibitors with $K_i$ values in the lower micromolar, preferably the nanomolar and even more preferably the picomolar range are contemplated. Likewise, agents with an $IC_{50}$ (if such a determination is applicable) for tyrosine kinase inhibition of 100 μM or less, more preferably of 10 μM or less, even more preferably of 1.0 μM or less or 0.1 μM or less, or most preferably 0.01 μM or less may be utilized as tyrosine kinase inhibitors. Indeed, inhibitors with $IC_{50}$ values in the lower micromolar, preferably the nanomolar and even more preferably the lower nanomolar range are contemplated. Thus, while the active agents are described herein, for convenience, as "tyrosine kinase inhibitors", it will be understood that such nomenclature is not intending to limit the subject of the invention to a particular mechanism of action.

Preferably, the tyrosine kinase inhibitors of the subject method or medical use will be small molecules, e.g., with molecular weights of 1000 g/mole or less, 500 g/mole or less, preferably of 400 g/mole or less, and even more preferably of 350 g/mole or less and even of 300 g/mole or less.

As used herein, the term "pharmaceutically acceptable" embraces both human and veterinary use: for example the term "pharmaceutically acceptable" embraces a veterinarily acceptable compound or a compound acceptable in human medicine and health care.

Inhibitors can be, for example, inhibitors of the tyrosine kinase activity of the KIAA0368-ROBO2 fusion protein, or alternatively inhibitors of the binding activity of the KIAA0368-ROBO2 to proteins with which they interact. Specific examples of such inhibitors can include, for example, anti-KIAA0368-ROBO2 antibodies, peptides, protein fragments, or small peptidyl protease inhibitors, or small non-peptide, organic molecule inhibitors which are formulated in a medium that allows introduction into the desired cell type. Alternatively, such inhibitors can be attached to targeting ligands for introduction by cell-mediated endocytosis and other receptor mediated events. Such methods are described further below and can be practiced by those skilled in the art given the KIAA0368-ROBO2 nucleotide and amino acid sequences described herein.

A further use of the KIAA0368-ROBO2 fusion protein is for the screening of potential antagonists for use as therapeutic agents, for example, for inhibiting binding to KIAA0368-ROBO2, as well as for screening for agonists. The KIAA0368-ROBO2 fusion protein, its immunogenic fragments, or oligopeptides thereof can be used for screening libraries of compounds, which are prospective agonists or antagonists in any of a variety of drug screening techniques. The fragment employed in such screening may be free in solution, affixed to a solid support, borne on a cell surface, or located intracellularly. The formation of binding complexes between a KIAA0368-ROBO2 fusion protein and the agent being tested is then measured.

A method provided for screening a library of small molecules to identify a molecule which binds a KIAA0368-ROBO2 fusion protein generally comprises: a) providing a library of small molecules; b) combining the library of small molecules with the KIAA0368-ROBO2 fusion protein, e.g. the polypeptide of SEQ ID NOS 1, or with a fragment thereof, under conditions which are suitable for complex formation; and c) detecting complex formation, wherein the presence of such a complex identifies a small molecule, which binds to the KIAA0368-ROBO2 fusion protein.

Suitable inhibitors of tyrosine kinases, which could be also useful as inhibitors of KIAA0368-ROBO2 fusion proteins, are well known in the prior art.

In a preferred embodiment, the present invention provides a method of treating a proliferative disease, based on the presence of the KIAA0368-ROBO2 fustion protein using tyrosine kinase inhibitors and/or antibodies and/or small nucleotides such as polynucleotide molecules having sequences that are antisense to mRNA transcripts.

Likewise, the invention provides the use of tyrosine kinase inhibitors and/or antibodies and/or small nucleotides such as polynucleotide molecules having sequences that are antisense to mRNA transcripts in such methods of treatment.

Moreover, tyrosine kinase inhibitors and/or antibodies and/or small nucleotides such as polynucleotide molecules having sequences that are antisense to mRNA transcripts are provided for use in the treatment of proliferative diseases.

The present invention further provides a method for diagnosing a proliferative disease in a subject comprising the steps of:
  determining the presence and/or expression of at least one fusion gene of KIAA0368-ROBO2 in a biological sample derived from said patient; and
  attributing the presence or expression of said fusion gene to the presence of a proliferative disease in said patient.

Said method of diagnosis may be accomplished by detecting the presence and/or expression of said fusion gene is detected by a hybridisation and/or an amplification assay. Such hybridisation and/or amplification assay may be selected from any suitable assay known in the art, for example an assay selected from the group consisting of polymerase chain reaction (PCR), real-time PGR, reverse transcriptase PCR (RT-PCR), fluorescent in situ hybridisation (FISH), chromogenic in situ hybridisation (CISH), break-apart in situ hybridisation (ba-FISH), and silver in situ hybridisation (SISH).

In a further aspect of the invention, there is provided a method for diagnosing a proliferative disease in a subject comprising the steps of
  determining the amount of at least one fusion protein of KIAA0368-ROBO2 in a biological sample; and
  comparing the detected amount of said fusion protein in the biological sample with an amount of said KIAA0368-ROBO2 fusion protein and/or ROBO2 protein and/or KIA0368 protein characteristic of a normal control subject;
wherein an elevated amount of said at least one fusion protein in said biological sample relative to the amount of said KIAA0368-ROBO2 fusion protein and/or ROBO2 protein and/or KIA0368 protein in the normal control is a positive indicator of the proliferative disease.

The term "proliferative disease" as used herein is interchangeable with cancer. Preferably, the proliferative disease according to the invention is a glioa, most preferably glioblastoma (GBM).

The term "subject" refers to a mammal which is afflicted with, or suspected to be afflicted with a proliferative disease such as glioma, most preferably glioblastoma (GBM). Preferably, "subject" refers to a human.

The term "biological sample" refers to any source of biological material, including, but are not limited to, peripheral blood, plasma, lymphocytes, cerebrospinal fluid, urine, saliva, epithelia, fibroblasts, cell extracts or any other sample comprising a KIAA0368-ROBO2 fusion protein, fusion gene and/or mRNA. The sample can be treated prior to use, such as preparing plasma from blood, diluting viscous fluids, and the like. Preferably, the plasma sample is treated with an anti-coagulant, such as EDTA.

In a further preferred embodiment of the invention, the biological sample is a tissue sample or a biopsy.

A "tissue sample" is derived or obtained from a subject (the patient suffering from a proliferative disease) and may be obtained via biopsy such as needle biopsy, surgical biopsy, bone marrow biopsy etc. A tissue sample includes a specimen of a proliferative diseases, i.e. cancer, parts of a cancer, cancer cells derived from a cancer (including cancer cell lines which may be derived from a cancer and which are grown in cell culture) and also the cancer mass as a whole, but also cancer cell lines as such, and cells and/or tissue which are/is derived from a subject and which are/is suspected of being cancerous or which are/is suspected of comprising cancerous cells. It is thus envisaged that the tissue sample may also comprise non-cancerous cells. For example cancer cells and/or (micro) metastases are frequently surrounded by healthy, i.e. non-cancerous tissue, i.e. the cancer cells could then form a subset of cells within the healthy tissue. A tissue sample thereby could comprise a subset of healthy (noncancerous) cells and a subset of cancerous cells. The term "sample" is interchangeable with "specimen".

According to a further embodiment of the present invention, the amount of the KIAA0368-ROBO2 fusion protein is detected either on the basis of the KIAA0368-ROBO2 protein level or the KIAA0368-ROBO2 mRNA level.

The amount of a KIAA0368-ROBO2 protein may be further detected using an antibody that specifically binds to said KIAA0368-ROBO2 protein.

As aforementioned, the KIAA0368-ROBO2 fusion protein shows tyrosine kinase activity. Accordingly, the amount of a KIAA0368-ROBO2 fusion protein may also be detected by measuring the tyrosine kinase activity in said biological sample.

The amount of a KIAA0368-ROBO2 fusion protein detected or quantified in a biological sample from a subject can be accomplished by any means known in the art. Such means may include, but are not limited to, for example by immunoturbidimetric assay, immunofluorescence, immunodiffusion, enzyme-linked immunosorbent assay (ELISA), radioimmunoassay (RIA), Western Blot, protein activity assay or, for the determination of the mRNA level, Northern Blot or polymerase chain reaction (PCR) analysis, for example real-time PCR. Also useful are high performance liquid chromatography (HPLC), mass spectrometry (MS) and gas chromatography (GC), as well as their various configurations, including gas chromatograph-mass spectrometry (GC-MS), liquid chromatography-mass spectrometry (LC-MS) and liquid-chromatography-tandem mass spectrometry (LC-MS/MS) systems.

Further preferably, the amount of a KIAA0368-ROBO2 fusion protein in the biological sample is detected using an antibody that binds to the KIAA0368-ROBO2 fusion protein in an immunoassay format. Thus, according to a preferred embodiment of the invention, there is provided a method of diagnosing a proliferative disease in a subject, the method comprising:

contacting said biological sample from said subject with an antibody that binds to a KIAA0368-ROBO2 fusion protein;

allowing the antibody and the a KIAA0368-ROBO2 fusion protein to form an immune complex; and detecting the amount of immune complex formed as an indication of the amount of a KIAA0368-ROBO2 fusion protein in said biological sample; and comparing the detected amount of a KIAA0368-ROBO2 fusion protein to the amount of said KIAA0368-ROBO2 protein and/or ROBO2 protein and/or KIAA0368 protein in a sample from normal control subject;

wherein a detected amount that is elevated relative to the normal control is a positive indicator of said proliferative disease.

In a preferred embodiment, said method is performed in vitro.

In a further preferred embodiment, said biological sample and/or normal control sample has already been obtained from said subject and/or normal control subject prior to conducting said method.

An "elevated amount" of a KIAA0368-ROBO2 fusion protein means that the amount of KIAA0368-ROBO2 detected in the samples of the subjects is greater than the mean amount of said KIAA0368-ROBO2 fusion protein characteristic of a normal control person beyond the range of experimental error, as known in the art. Preferably, the amount of the KIAA0368-ROBO2 fusion protein detected in the samples of the subjects is 10% greater than said mean amount of said KIAA0368-ROBO2 fusion protein characteristic of a normal control person. More preferably, the amount of a KIAA0368-ROBO2 fusion protein detected in the samples of the subjects is 25% greater, or, even more preferred 50% or 75% greater than said mean amount of said KIAA0368-ROBO2 fusion protein characteristic of a normal control person. Most preferably, the amount of KIAA0368-ROBO2 fusion protein detected in the samples of the subjects is several times greater than said mean amount of the KIAA0368-ROBO2 fusion protein characteristic of a normal control person, e.g. 2, 3, 4, 5, 6, 7, 8, 9, 10 or more times greater.

In an alternative embodiment, the presence of the KIAA0368-ROBO2 fusion protein can be detected by an elevated amount of the ROBO2 protein only. Accordingly, an "elevated amount" may be related to the ROBO2 protein alone and shall mean that the amount of ROBO2 detected in the samples of the subjects is greater than the mean amount of said ROBO2 protein characteristic of a normal control person beyond the range of experimental error, as known in the art. Preferably, the amount of the ROBO2 protein detected in the samples of the subjects is 10% greater than said mean amount of said ROBO2 protein characteristic of a normal control person. More preferably, the amount of a ROBO2 protein detected in the samples of the subjects is 25% greater, or, even more preferred 50% or 75% greater than said mean amount of said ROBO2 protein characteristic of a normal control person. Most preferably, the amount of ROBO2 protein detected in the samples of the subjects is several times greater than said mean amount of the ROBO2 protein characteristic of a normal control person, e.g. 2, 3, 4, 5, 6, 7, 8, 9, 10 or more times greater.

Suitable inhibitors of ROBO2-related diseases could also be inhibitors of KIAA0368-ROBO2 expression. Further preferred according to the invention is thus a method of screening for an agent that inhibits a KIAA0368-ROBO2 related cancer in a subject comprising obtaining a tissue sample from a subject with a KIAA0368-ROBO2 related cancer;

contacting the tissue sample with said agent;

extracting mRNA from the tissue sample;

conducting an RT-PCR reaction on the mRNA from the tissue sample;

wherein the RT-PCR reaction comprises a reverse primer capable of specifically hybridizing to one or more sequences and at least one forward primer; and wherein a decrease in the amount of amplification product relative to an untreated control indicates an agent that can inhibit an KIAA0368-ROBO2 related cancer.

The KIAA0368-ROBO2 fusion gene and/or fusion protein of the invention is further useful for diagnosing and/or monitoring of tumor progression, preferably of the progression of brain tumors.

In a further embodiment, the KIAA0368-ROBO2 fusion gene and/or fusion protein of the invention can be used for the subclassification of brain tumors and other proliferative diseases. The KIAA0368-ROBO2 fusion gene and/or fusion protein of the invention is particularly suitable for the classification of gliomas, i.e. into the three main subgroups astrocytomas, oligodendrogliomas, and mixed gliomas (oligoastrocytomas) according to the current WHO classification. More preferably, the KIAA0368-ROBO2 fusion gene and/or fusion protein of the invention is suitable to distinguish between four malignancy grades according to the current WHO classification (WHO grades I-IV). Most preferably, the KIAA0368-ROBO2 fusion gene and/or fusion protein of the invention can be used for the differentiation and/or subclassification between glioblastoma multiforme (WHO grade IV) and anaplastic glioma (WHO grade III) with either oligodendroglial, astrocytic or both features.

Accordingly, in a preferred embodiment, the present invention further relates to the use of KIAA0368-ROBO2 fusion gene and/or fusion protein, which preferably have a sequence selected from one of SEQ ID NOS 1 to 4 for diagnosing and/monitoring of tumor progression, preferably of the progression of brain tumors. In a further preferred embodiment, the present invention relates to the use of KIAA0368-ROBO2 fusion gene and/or fusion protein, which preferably have a sequence selected from one of SEQ ID NOS 1 to 4 for the subclassification of brain tumors and other proliferative diseases.

Accordingly, also the methods and kit of the present invention, which are based on the use of the KIAA0368-ROBO2 fusion gene and/or fusion protein are suitable for use in diagnosing and/monitoring of tumor progression, preferably of the progression of brain tumors and/or the subclassification of brain tumors and other proliferative diseases.

The invention further provides a method for determining whether a subject suffering from a proliferative diseases is susceptible to treatment with a tyrosine kinase inhibitor, preferably an inhibitor of the ROBO2 kinase activity, comprising detecting the expression of a KIAA0368-ROBO2 fusion protein in biological sample of said subject, wherein an elevated amount of a KIAA0368-ROBO2 fusion protein indicates that said subject is susceptible to treatment with a tyrosine kinase inhibitor.

The term "susceptible to treatment with a tyrosine kinase inhibitor" when used herein means that a tyrosine kinase inhibitor, preferably a ROBO2 kinase inhibitor may potentially have a therapeutic effect in a patient to whom a tyrosine kinase inhibitor is and/or will be administered. Said term when used herein is equivalent to the term "sensitive to treatment with a tyrosine kinase inhibitor" or "responsive to treatment with a tyrosine kinase inhibitor".

By "therapeutic effect" or "therapeutically effective" is meant that a tyrosine kinase, which is preferably an inhibitor of the ROBO2 kinase activity, may produce the therapeutic effect for which it is administered. Preferably, a therapeutic effect includes the reduction, stabilization or inhibition of progression of a cancer-associated symptom, such as cancer size, number of metastases or other symptoms which are caused by/associated with the presence and/or progression of a cancer or proliferative disease, preferably a glioma such as GBM. The response includes a complete response, a partial response, a stable disease (without progression or relapse), and/or a response with a later relapse of the patient. Preferably, as described herein the ROBO2 kinase inhibitor may affect that cancer cells will undergo cell death thereby, ameliorating and/or treating a cancer of a patient provided that said cancer cells express the ROBO2 protein, particularly the KIAA0368-ROBO2 fusion protein. The therapeutic effect of the respective methods or method steps of the present invention may be detectable by all established methods and approaches which will indicate a therapeutic effect. Alternatively, it is also envisaged that cancer markers in the serum of the patient (if present) are detected in order to diagnose whether or not the therapeutic approach is effective. The skilled person is aware of numerous other ways which will enable him or her to observe a therapeutic effect of a ROBO2 kinase inhibitor.

Diagnostic kits for carrying out the assays for diagnosing a proliferative disease in a subject are also provided. Thus, the present invention can be practiced using a diagnostic kit that includes at least one antibody specific for a KIAA0368-ROBO2 fusion protein, as described herein as well as any reagents necessary for the detection of antibody-KIAA0368-ROBO2 binding immune complexes. Generally, the kit may include a single antibody that specifically recognizes a KIAA0368-ROBO2 fusion protein. On the other hand, the kit may include a primary antibody that specifically recognizes a KIAA0368-ROBO2 fusion protein, as well as a secondary antibody that is conjugated with a signal-producing label and is capable of binding to the primary antibody, or at a site different from the site where the primary antibody binds. The signal-producing label linked to the secondary antibody may be, but is not limited to, an enzyme, such as horseradish peroxidase or alkaline phosphatase. The kits may further comprise other reagents for carrying out the assay such as buffers, a solid support, solutions and the like. The kit may also contain instructions for carrying out the method of the invention using one or more antibodies in diagnostic assays.

EXAMPLES OF THE INVENTION

1. Detection of Translocation Between Chromosomes 3 and 9

1.1 Cell Culture

Primary cell cultures from a tumor containing the chromosomal translocation and a tumor from the same patient without the translocation as well as the U87MG cell line of glioblastoma origin were cultured in tissue culture flasks in a humidified incubator (95% RH, 37° C., 5% CO2). The cells were cultured in Dulbecco's Modified Eagle's Minimal Essential Medium (DMEM) (GIBCO, Carlsbad, USA) supplemented with 20% fetal calf serum (FCS; Biochrom AG, Berlin, Germany), 4× Minimal Essential Medium Non-Essential Amino Acids (MEM NEAA; Gibco, Carlsbad, USA), 10 mM HEPES (PAA, Cölbe, Germany) and 100 U/ml Penicillin-0.1 mg/ml Streptomycin (GIBCO, Carlsbad, USA).

1.2 DNA Extraction

DNA was extracted from fresh frozen tumor material and primary cell cultures by phenol:chloroform extraction using standard protocols. RNA was extracted using the QIAGEN miRNeasy Mini Kit according to the manufacturer's instructions (QIAGEN, Hilden, Germany). RNA quality was assessed using the Agilent RNA 6000 Nano chip on a 2100 Bioanalyzer using the RNA Integrity Number (RIN) value.

1.3 Spectral Karyotyping (SKY)

For preparation of metaphase chromosomes cells were treated with colcemid for 60 min at a concentration of 0.035 µg ml-1, incubated in 0.075M 1 KCl for 20 minutes at 37° C., and fixed in a freshly prepared mixture of methanol/acetic acid (3:1) at room temperature. Cell suspension was dropped onto glass slides. Spectral karyotyping (SKY) analysis was performed as described previously (Schröck et al. 1996). Metaphase chromosomes were hybridized for 3 days with a self-made SKY hybridization probe cocktail for human chromosomes as described (Schrock et al., 1997). SKY images of about 20 metaphase chromosomes per cell line stained with a mixture of 5 fluorochromes (green, orange, red, far-red, and near-infrared) were captured using an DMRXA epifluorescence microscope (Leica Mikrosysteme Vertrieb GmbH, Wetzlar, Germany) with an HCX PL SAPO 63x/1.30 oil objective (Leica Mikrosysteme Vertrieb GmbH, Wetzlar, Germany) with the SpectraCube® system (Applied Spectral Imaging, Migdal HaEmek, Israel) and the SKYView® imaging software (Applied Spectral Imaging, Migdal HaEmek, Israel).

1.4 Array Comparative Genome Hybridization (aCGH)

Extracted DNA was hybridized onto Agilent's SurePrint G3 Human CGH Microarray Kit 2×400K (Design ID 021850, Agilent, Santa Clara, Calif., USA) according to the manufacturer's instructions with the exception that the labeling of reference and test DNA was reversed. The chips were scanned using an Agilent microarray scanner. Raw data were extracted and processed using Feature Extraction 9.5 software (Agilent) and normalization was done using default settings. Agilent's Genomic Workbench Standard Edition 5.0.14 was used to determine deleted and amplified regions based on the draft of the reference human genome (NCBI36/hg28). Copy number variations (CNV) were computed using the ADM-2 algorithm and a minimum of five consecutive probes had to be affected to report a CNV at a threshold of 5.9. All results were additionally checked by eye for confirmation.

1.5 Results

Figure 2:
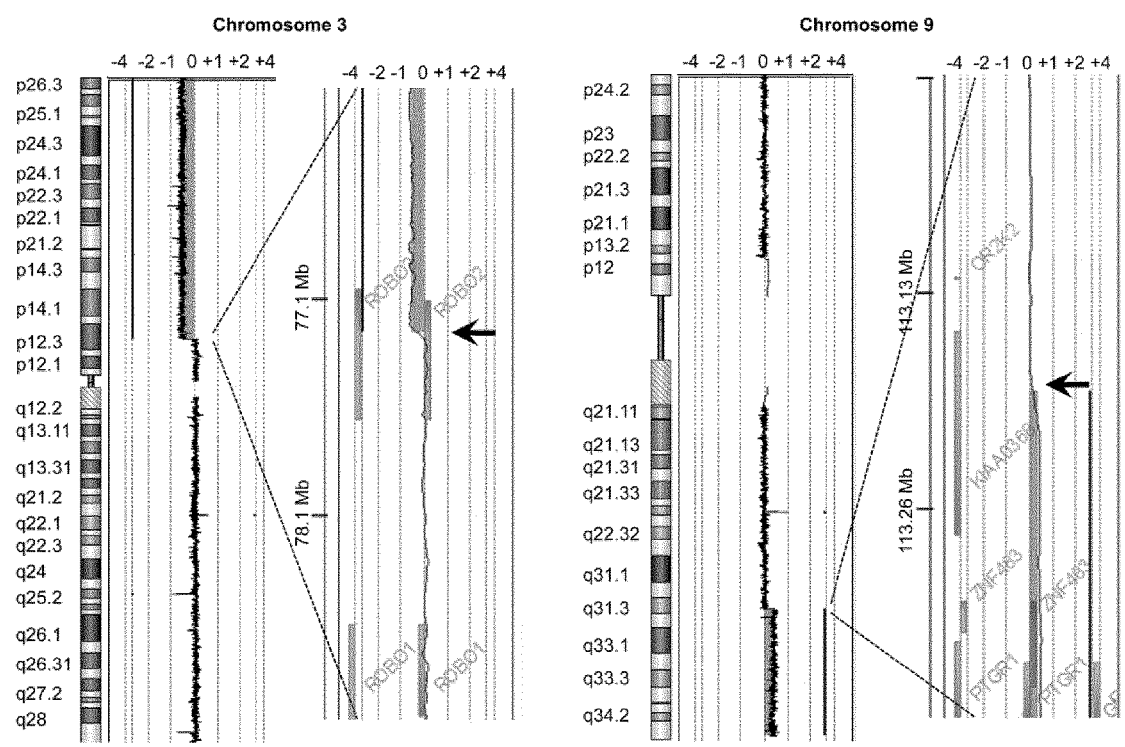
FIG. 2 shows the result of Array Comparative Genome Hybridization (aCGH) as it appears in Agilent's CytoGenomics software on GBM Focus 1. On the left is chromosome 3 and the right is chromosome 9. For each, the left shows the whole chromosome and the right is an enlargement of the breakpoint area. Log ratios along the chromosomal regions ranging from −4 to +4 are displayed as a jagged line around 0 and copy number losses (log ration <−0.5) are indicated by a line to the left the log ratios while copy number gains (>0.5) are indicated by a line to the right of the log ratios. The unbalanced translocation t(3;9) led to partial loss of the short arm of chromosome 3 (del3p12.3-pter) and partial gain of the long arm of chromosome 9 (dup9q31.3-qter). The breakpoint regions are enlarged on the rights with genes (Robo2 and Kiaa0368) displayed as grey boxes and the breakage points are indicated by arrows.

Using spectral karyotyping (SKY) cases of GBM from a patient presenting with multifocal GBM with an unbalanced translocation between chromosomes 3 and 9 could be detected (hereafter named Focus 1; FIG. 1). Using array comparative genome hybridization (aCGH), a method that can detect genomic gains and losses of more than 10 kb, it could be detected that the breakpoints were located within the genes ROBO2 and KIAA0368 on chromosomes 3 and 9 respectively (FIG. 2). More specifically, the latter parts of ROBO2 were under the control of the promoter of KIAA0368.

2. Amplification of the Fusion Transcript 2.1 Reverse Transcriptase Polymerase Chain Reaction (RT-PCR)

Extracted total RNA was reverse transcribed into cDNA using the SuperScript VILO cDNA Synthesis Kit (Invitrogen, Carlsbad, USA). The synthesis was carried out according to the manufacturer's protocol. The polymerase chain reaction was carried out using the kit from Qiagen (Hilden, Germany) with the addition of Q-solution and Hot Start Taq Polymerase. In order to amplify the region spanning the fusion region, 10 µM of each of a primer binding on ROBO2 and another binding KIAA0368 were used (Forward (KIAA0368): TTGGATTGCTCGTTCTTTCA (SEQ ID NO 7), Reverse (ROBO2): TTTTCCAACCCGATTCTCAG (SEQ ID NO 6)). Ten nanograms of cDNA was used per reaction and the PCR was carried out with the following program: initial denaturation at 95° C. for 15 minutes followed by 34 cycles of 95° C. for 30 seconds, an annealing step at a temperature defined by the melting temperature of the primers for 30 seconds, and elongation at 72° C. for 45 seconds. A final elongation step of 72° C. for 10 minutes followed. The PCR products were run on a 2% agarose gel at 110V for an hour and the bands visualized under ultraviolet light.

2.2 Results

Figure 3:
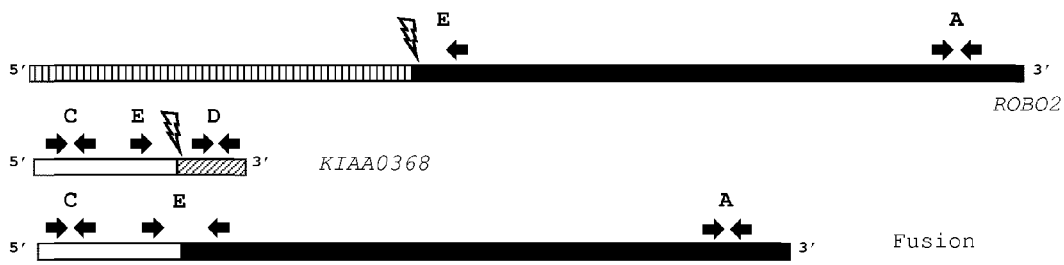
FIG. 3 shows a Schematic diagram of ROBO2 (black and vertical striped) and KIAA0368 (white and diagonally striped) transcripts. Solid areas are conserved in the fusion transcript while striped regions are lost. The primer pairs are indicated by black arrows. Primer pair E will only give an amplicon in the presence of the fusion transcript.
Figure 4:
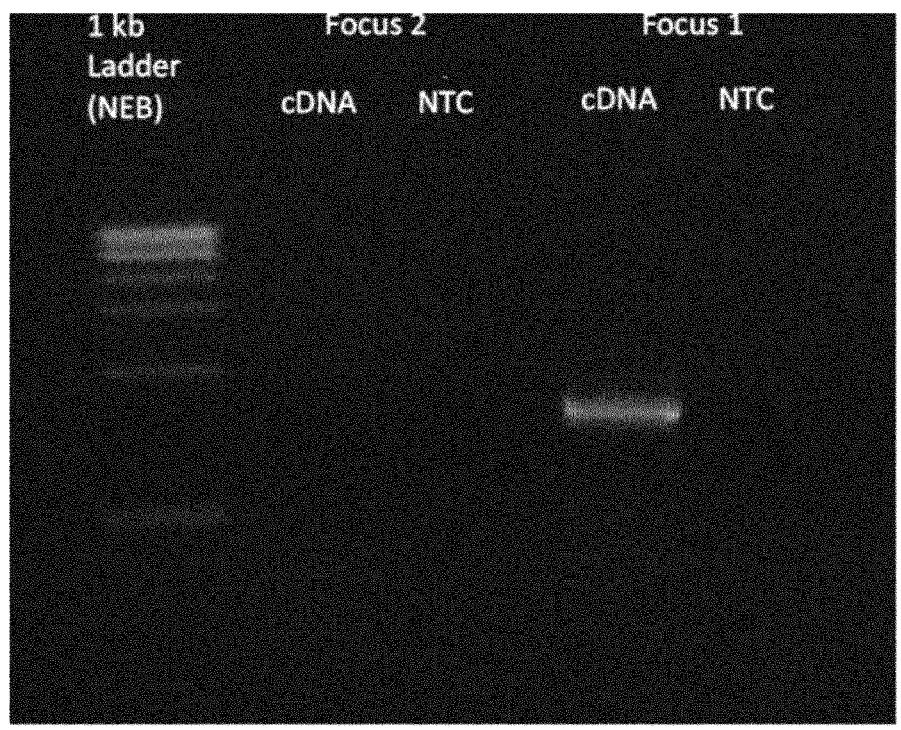
FIG. 4 shows the results of polymerase chain reaction (PCR) on cDNA from GBM Focus 1 and GBM Focus 2. mRNA was extracted from each focus, reverse transcribed into cDNA and amplified using the primers described above (table 1). Amplicons were run on agarose gel and were observed only in the case of cDNA from Focus 1 and not Focus 2. NTC refers to non-template control, cases were no cDNA was loaded but replaced with water.

To identify the fusion transcript KIAA0368-ROBO2 and better characterize the regions involved in the fusion, it has been attempted to amplify this transcript by polymerase chain reaction (PCR). PCR uses 'primer pair': short oligonucleotides that bind to a specific region and create a template to build a complementary strand of DNA to the region of interest. Through several cycles of heating and cooling, it is possible to create millions of copies of this DNA. Therefore primers were designed that are capable of binding to regions on either side of the fusion point (thus, one primer binds to the ROBO2 transcript and one to the KIAA0368 transcript; see FIG. 3) and which only give a result if the fusion is found in the cell (primer pairs used are provided in Table 1 below). The result was checked against the other GBM focus (hereafter called Focus 2) obtained from a patient and an established cell line of GBM origin (U87-MG). The PCR product could be observed only in Focus 1 and not in Focus 2 or the cell line (FIG. 4).

TABLE 1

Primers used for amplification of ROBO2 and KIAA0368. ROBO2 reverse primer (ROBO2_E_1_R) and KIAA0368 (KIAA_E_2_F) forward primer were used to obtain an amplicon in the tumor with the fusion.

| Name | Sequence | Target | SEQ ID NO. |
|---|---|---|---|
| ROBO_E_1_F | GCAGACTTGCCAAGAGGAAG | PCR on cDNA, binding on ROBO2 | 5 |
| ROBO_E_1_R | TTTTCCAACCCGATTCTCAG | PCR on cDNA, binding on ROBO2 | 6 |
| KIAA_E_2_F | TTGGATTGCTCGTTCTTTCA | PCR on cDNA, binding on KIAA0368 | 7 |
| KIAA_E_2_R | TGAGGGATCTGGCTTTACCA | PCR on cDNA, binding on KIAA0368 | 8 |

3. Sequencing of the PCR Products 3.1 Sanger Sequencing

The PCR amplicons described above were cleaned using the enzyme exonuclease I. In summary, rAPID buffer, SAP buffer (Roche, Mannheim, Germany), exonuclease I (NEB, Ipswich, USA) and nuclease-free water was added to the PCR products and placed in a thermal cycler at 37° C. for an hour followed by 20 minutes at 80° C. The products were then labeled using dideoxynucleotides (ddNTP) in a PCR reaction with the BigDye Terminator v.3.1 Cycle Sequencing Kit (Applied Biosystems, Life Technologies, Carlsbad, USA) using both forward and reverse primers in a thermocycler with a program consisting of 26 cycles of 96° C. for 10 seconds followed by 5 seconds at 60° C. and 4 minutes at the same temperature. The products were cleaned by centrifuging them through a sephadex column (illustra Sephadex G-50 DNA grade, GE Healthcare, Piscataway, N.J., USA) and then were loaded in a sequencer (3130xl Genetic Analyzer, Applied Biosystems, Carlsbad, USA).

3.2 Results

Figure 6:
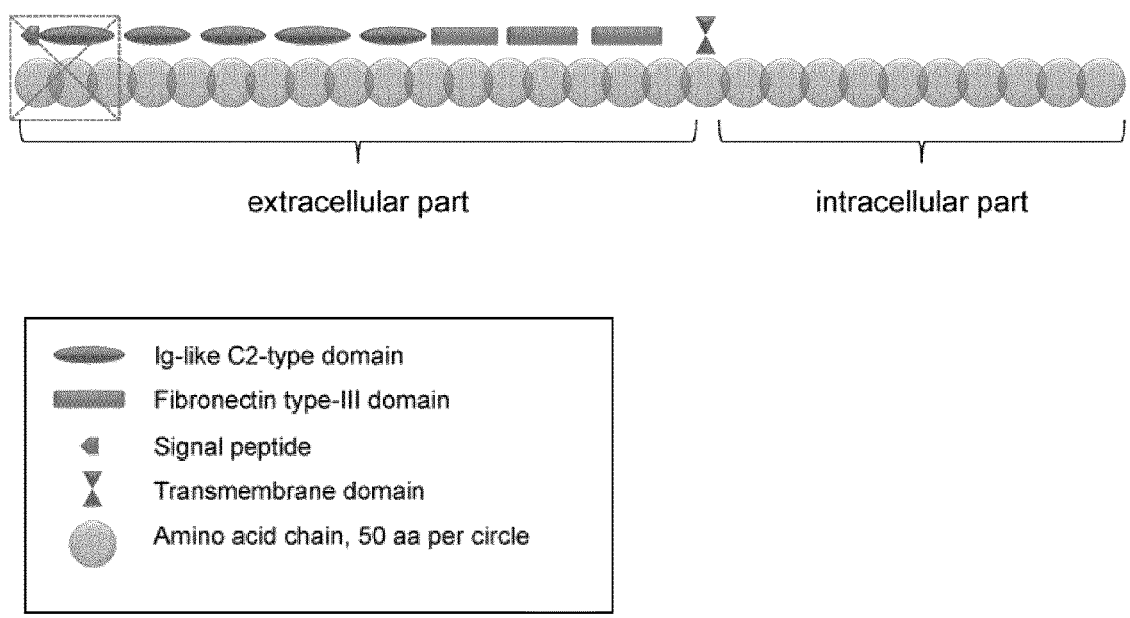
FIG. 6 shows an illustration of the functional domains of ROBO2. The square with a cross in the middle indicates the regions that are lost in the fusion transcript.

To locate the exact regions of both genes involved in the translocation, the PCR products as described in example 2 were sequenced using Sanger sequencing. The results indicated that the transcript was formed by the first 26 exons of KIAA0368 and the last 22 exons of ROBO2 (FIG. 5). Therefore, the first Ig-like domain required to bind the ligand was missing in ROBO2 in this transcript (FIG. 6).

4. Quantitative PCR 4.1 Reverse Transcriptase Quantitative PCR (RT-qPCR)

Extracted total RNA was reverse transcribed into cDNA using the SuperScript VILO cDNA Synthesis Kit (Invitrogen, Carlsbad, USA). The synthesis was carried out according to the manufacturer's protocol. A ten-time serial dilution of the primers was used to detect their efficiency (E). The QuantiFast SYBR Green PCR Kit (Qiagen, Hilden, Germany) was used for the reaction according to the manufacturer's instructions in 96-well PCR plates in a 7300 Prism thermocycler (Applied Biosystems, Carlsbad, USA). The CT values were determined as the cycle at which the amplification curve crosses a predefined threshold. All values were normalized to the geometric mean of the CT values of the expression of two reference genes (GAPDH and ARF1). The fold-change was calculated according to the following formula: (E_test^CT-E_control^CT)/(E_reft^CT-E_refc^CT) where 'test' indicates the tumor with the translocation, 'control' the tumor without the translocation, 'reft' denotes the geometric mean of the reference genes for the 'test' condition and 'refc' the geometric mean of the reference genes for the 'control' condition.

4.2 Results

Figure 7:
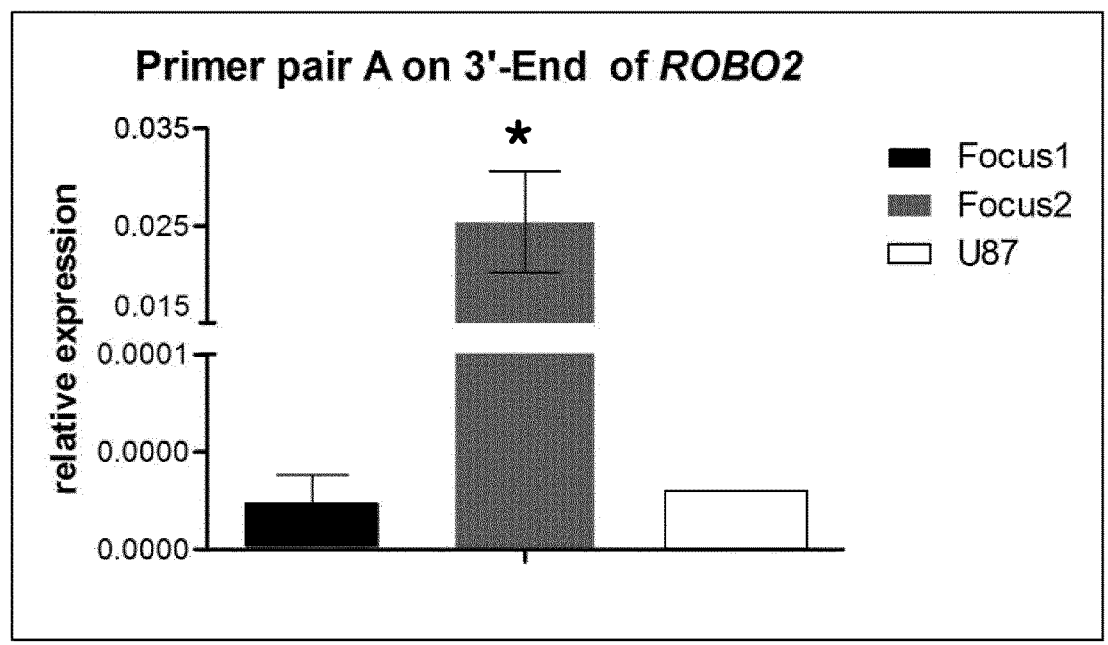
FIG. 7 shows a histogram with qPCR results reported as relative expression of ROBO2 transcript. mRNA was extracted from all samples and reverse transcribed to cDNA. qPCR was carried out and the Ct value reported as the cycle at which the fluorescence crosses a certain preset threshold. The Ct value of each sample was normalized to that of two reference genes (Arf-1 and GAPDH). The expression of ROBO2 in GBM Focus 1 is around 10-fold more than that in GBM Focus 2 or U87 cell line. Asterisk indicates significance at p=0.05.

In order to test the effect that the fusion has on the transcriptional level of ROBO2, a quantitative PCR (qPCR) was performed on Focus 1 against Focus 2 and the U87-MG cell line. The results showed that ROBO2 transcriptional levels were significantly up-regulated (almost 10-fold) in Focus 1 when compared to Focus 2 and the U87-MG cell line (FIG. 7). The transcriptional level of ROBO2 in Focus 1 was comparable to that of KIAA0368 highlighting the influence of the latter's promoter on ROBO2 levels in the cells.

5. Tyrosine Kinase Assay

The compounds according to the invention can be tested for ROBO2 kinase inhibitory activity. Kinase inhibitory activity can be measured by using Z-Lyte Kinase Assay Kit (Invitrogen). Specifically, the compounds of the invention were diluted with an aqueous solution of 4% DMSO to obtain solutions with concentrations in the range of 1 to 0.0001 µM. The ROBO2 kinase or the KIAA0368-ROBO2 kinase was diluted to 1 to 10 ng/assay, and ATP was diluted to form a kinase buffer (50 mM HEPES, pH 7.4; 10 mM MgCl$_2$; 1 mM EDTA; and 0.01% BRIJ-35) by calculating an approximate Kd value. The assays were performed in 384-well polystyrene flat-bottomed plates. Peptide substrate having a suitable concentration, 10 µl of mixed kinase solution and 5 µl of ATP solution having a concentration of 5 to 300 µM were added to 5 µl of the diluted solution of the compound, and allowed to react in a mixer for 60 minutes at room temperature. After 60 minutes, 10 µl of fluorescent labeling reagents was added to each mixture so as to allow fluorescent labeling of peptide substrates, followed by adding a finishing solution to complete the reaction. The fluorescence level was determined with a Molecular Device at 400 nm (excitation filter) and 520 nm (emission filter). The kinase inhibitory activities of the compounds were calculated in phosphorylation rates between 0~100% against the control group (staurosporine or each of kinase inhibitor) according to the reference protocol of the kit, and percentage inhibition was determined and plotted against concentration (x-axis) to calculate 50% inhibitory concentration (IC50). The calculation and analysis of IC50 was carried out by using Microsoft Excel.

The invention claimed is:

1. A method for detecting a proliferative disease in a subject comprising the steps of
   obtaining a biological sample from the subject;
   contacting the biological sample with an antibody that binds to a polypeptide having the amino acid sequence of SEQ ID NO: 1;
   detecting an amount of an immune complex present in said biological sample with said antibody;
   determining the amount of at least one KIAA0368-ROBO2 fusion protein in the detected immune complex;
wherein an elevated level of KIAA0368-ROBO2 fusion protein in the biological sample compared to a control level of any one or any combination of a KIAA0368-ROBO2 fusion protein, a ROBO2 protein, and a KIAA0368 protein is a positive indicator of said proliferative disease.

2. The method for detecting a proliferative disease according to claim 1, comprising:
   contacting the biological sample with an antibody that binds to a polypeptide encoded by the nucleic acid sequence of SEQ ID NO: 2;
   detecting an amount of an immune complex with said antibody present in said biological sample;
   determining the amount of at least one KIAA0368-ROBO2 fusion protein in the detected immune complex; and
wherein an elevated level of KIAA0368-ROBO2 fusion protein in the biological sample compared to a control level of any one or any combination of a KIAA0368-ROBO2 fusion protein, a ROBO2 protein, and a KIAA0368 protein is a positive indicator of said proliferative disease.

3. The method according to claim 1 wherein the proliferative disease is a glioma.

* * * * *

SEQUENCE LISTING

```
<160> NUMBER OF SEQ ID NOS: 8

<210> SEQ ID NO 1
<211> LENGTH: 2352
<212> TYPE: PRT
<213> ORGANISM: Homo sapiens

<400> SEQUENCE: 1

Met Thr Ser Arg Thr Lys Arg Arg Gln Lys Val Lys Ile Ser Ile Ser
1               5                   10                  15

Lys Ile Asn His Ser Ser Tyr Arg Lys Glu His Arg Pro Phe Trp Glu
            20                  25                  30

His Gln Pro Pro Pro His Gln Asn Trp Ala Val Gly Gly Arg Cys Gly
        35                  40                  45

Ala Gly Ala Arg Pro Gly Leu Ser Gln Arg Arg Gly Arg Glu Val Arg
    50                  55                  60

Arg Glu Ala Gln Gly Gly Ala Ser Ser Arg Arg Leu Arg Ala Arg Leu
65                  70                  75                  80

Tyr Phe Ser Glu Ser Thr Ser Leu Pro Leu Asp Arg Arg Gly Ser Pro
                85                  90                  95

Gly Pro Leu Gly Pro Ala Pro His Gly Leu Arg Arg Ala Ala Pro Arg
            100                 105                 110

Gly Pro Ala Arg Arg Thr Pro Arg Ser Thr Ala Leu Thr Ser Arg Arg
        115                 120                 125

Arg Ala Gln Arg Pro Arg His Gly Asp Arg Leu Arg Leu Arg Ser Glu
    130                 135                 140

Ala Arg Pro Arg Ala Ala Gly Asp Trp Pro Cys Ala Arg Gly Gly Ala
145                 150                 155                 160

Val Arg Pro Gly Arg Pro His Arg Pro Pro Arg Val Glu Ser Ala Arg
                165                 170                 175

Gly Ala His Ala Gly Arg Ala Ala Thr Asp Gln Leu Glu Arg Val Phe
            180                 185                 190

Leu Arg Leu Gly His Ala Glu Thr Asp Glu Gln Leu Gln Asn Ile Ile
```

```
            195                 200                 205
Ser Lys Phe Leu Pro Val Leu Leu Lys Leu Ser Ser Thr Gln Glu
210                 215                 220

Gly Val Arg Lys Val Met Glu Leu Leu Val His Leu Asn Lys Arg
225                 230                 235                 240

Ile Lys Ser Arg Pro Lys Ile Gln Leu Pro Val Glu Thr Leu Leu Val
                245                 250                 255

Gln Tyr Gln Asp Pro Ala Ala Val Ser Phe Val Thr Asn Phe Thr Ile
                260                 265                 270

Ile Tyr Val Lys Met Gly Tyr Pro Arg Leu Pro Val Glu Lys Gln Cys
                275                 280                 285

Glu Leu Ala Pro Thr Leu Leu Thr Ala Met Glu Gly Lys Pro Gln Pro
290                 295                 300

Gln Gln Asp Ser Leu Met His Leu Leu Ile Pro Thr Leu Phe His Met
305                 310                 315                 320

Lys Tyr Pro Val Glu Ser Ser Lys Ser Ala Ser Pro Phe Asn Leu Ala
                325                 330                 335

Glu Lys Pro Lys Thr Val Gln Leu Leu Leu Asp Phe Met Leu Asp Val
                340                 345                 350

Leu Leu Met Pro Tyr Gly Tyr Val Leu Asn Glu Ser Gln Ser Arg Gln
                355                 360                 365

Asn Ser Ser Ser Ala Gln Gly Ser Ser Asn Ser Gly Gly Gly Ser
370                 375                 380

Gly Ile Pro Gln Pro Pro Gly Met Ser Phe Tyr Ala Ala Lys Arg
385                 390                 395                 400

Val Ile Gly Asp Asn Pro Trp Thr Pro Glu Gln Leu Glu Gln Cys Lys
                405                 410                 415

Leu Gly Ile Val Lys Phe Ile Glu Ala Glu Gln Val Pro Glu Leu Glu
                420                 425                 430

Ala Val Leu His Leu Val Ile Ala Ser Ser Asp Thr Arg His Ser Val
                435                 440                 445

Ala Thr Ala Ala Asp Leu Glu Leu Lys Ser Lys Gln Ser Leu Ile Asp
450                 455                 460

Trp Asn Asn Pro Ala Ile Ile Asn Lys Met Tyr Lys Val Tyr Leu Gly
465                 470                 475                 480

Asp Ile Pro Leu Lys Thr Lys Glu Gly Ala Val Leu Lys Pro Glu Leu
                485                 490                 495

Lys Arg Asp Pro Val Ser Thr Arg Val Lys Leu Lys Ile Val Pro His
                500                 505                 510

Leu Leu Arg Ser Arg Gln Ala Ala Glu Thr Phe Pro Ala Asn Ile Gln
                515                 520                 525

Val Val Tyr Asp Gly Leu Phe Gly Thr Asn Thr Asn Ser Lys Leu Arg
                530                 535                 540

Thr Leu Ser Leu Gln Phe Val His His Ile Cys Ile Thr Cys Pro Glu
545                 550                 555                 560

Ile Lys Ile Lys Pro Leu Gly Pro Met Leu Leu Asn Gly Leu Thr Lys
                565                 570                 575

Leu Ile Asn Glu Tyr Lys Glu Asp Pro Lys Leu Leu Ser Met Ala Tyr
                580                 585                 590

Ser Ala Val Gly Lys Leu Ser Ser Arg Met Pro His Leu Phe Thr Lys
                595                 600                 605

Asp Ile Ala Leu Val Gln Gln Leu Phe Glu Ala Leu Cys Lys Glu Glu
610                 615                 620
```

-continued

Pro Glu Thr Arg Leu Ala Ile Gln Glu Ala Leu Ser Met Met Val Gly
625                 630                 635                 640

Ala Tyr Ser Thr Leu Glu Gly Ala Gln Arg Thr Leu Met Glu Ala Leu
            645                 650                 655

Val Ala Ser Tyr Leu Ile Lys Pro Glu Val Gln Val Arg Gln Val Ala
        660                 665                 670

Val Lys Phe Ala Ser Thr Val Phe Pro Ser Asp His Ile Pro Ser Arg
    675                 680                 685

Tyr Leu Leu Leu Ala Ala Gly Asp Pro Arg Glu Glu Val His Gly
690                 695                 700

Glu Ala Gln Arg Val Leu Arg Cys Leu Pro Gly Arg Asn Arg Lys Glu
705                 710                 715                 720

Ser Thr Ser Glu Gln Met Pro Ser Phe Pro Glu Met Val Tyr Tyr Ile
            725                 730                 735

Gln Glu Lys Ala Ser His Arg Met Lys Thr Pro Val Lys Tyr Met Thr
        740                 745                 750

Gly Thr Thr Val Leu Pro Phe Asn Pro Ala Ala Phe Gly Glu Ile Val
    755                 760                 765

Leu Tyr Leu Arg Met Cys Leu Ala His Ser Ala Gly Val Val Pro Thr
770                 775                 780

Ser Gln Ser Leu Ala Asp Met Gln Asp His Ala Pro Ala Ile Gly Arg
785                 790                 795                 800

Tyr Ile Arg Thr Leu Met Ser Ser Gly Gln Met Ala Pro Ser Ser Ser
            805                 810                 815

Asn Lys Ser Gly Glu Thr Asn Pro Val Gln Ile Tyr Ile Gly Leu Leu
        820                 825                 830

Gln Gln Leu Leu Ala Gly Val Gly Gly Leu Pro Val Met Tyr Cys Leu
    835                 840                 845

Leu Glu Ala Val Ser Val Tyr Pro Glu Lys Leu Ala Thr Lys Phe Val
850                 855                 860

Asp Lys Thr Glu Trp Ile Lys Ser Leu Met Asn Asn Ser Lys Glu Glu
865                 870                 875                 880

Met Arg Glu Leu Ala Ala Leu Phe Tyr Ser Val Val Ser Thr Val
            885                 890                 895

Ser Gly Asn Glu Leu Lys Ser Met Ile Glu Gln Leu Ile Lys Thr Thr
        900                 905                 910

Lys Asp Asn His Ser Pro Glu Ile Gln His Gly Ser Leu Leu Ala Leu
    915                 920                 925

Gly Phe Thr Val Gly Arg Tyr Leu Ala Lys Lys Met Arg Met Ser
930                 935                 940

Glu Gln Gln Asp Leu Glu Arg Asn Ala Asp Thr Leu Pro Asp Gln Glu
945                 950                 955                 960

Glu Leu Ile Gln Ser Ala Thr Glu Thr Ile Gly Ser Phe Leu Asp Ser
            965                 970                 975

Thr Ser Pro Leu Leu Ala Ile Ala Ala Cys Thr Ala Leu Gly Glu Ile
        980                 985                 990

Gly Arg Asn Gly Pro Leu Pro Ile Pro Ser Glu Gly Ser Gly Phe Thr
    995                 1000                1005

Lys Leu His Leu Val Glu Ser Leu Leu Ser Arg Ile Pro Ser Ser
    1010                1015                1020

Lys Glu Thr Asn Lys Met Lys Glu Arg Ala Ile Gln Thr Leu Gly
    1025                1030                1035

```
Tyr Phe Pro Val Gly Asp Gly Asp Phe Pro His Gln Lys Leu Leu
1040                1045                1050

Leu Gln Gly Leu Met Asp Ser Val Glu Ala Lys Gln Ile Glu Leu
1055                1060                1065

Gln Phe Thr Ile Gly Glu Ala Ile Thr Ser Ala Ala Ile Gly Thr
1070                1075                1080

Ser Ser Val Ala Ala Arg Asp Ala Trp Gln Met Thr Glu Glu Glu
1085                1090                1095

Tyr Thr Pro Pro Ala Val Leu Arg Asp Asp Phe Arg Gln Asn Pro
1100                1105                1110

Thr Asp Val Val Val Ala Ala Gly Glu Pro Ala Ile Leu Glu Cys
1115                1120                1125

Gln Pro Pro Arg Gly His Pro Glu Pro Thr Ile Tyr Trp Lys Lys
1130                1135                1140

Asp Lys Val Arg Ile Asp Asp Lys Glu Glu Arg Ile Ser Ile Arg
1145                1150                1155

Gly Gly Lys Leu Met Ile Ser Asn Thr Arg Lys Ser Asp Ala Gly
1160                1165                1170

Met Tyr Thr Cys Val Gly Thr Asn Met Val Gly Glu Arg Asp Ser
1175                1180                1185

Asp Pro Ala Glu Leu Thr Val Phe Glu Arg Pro Thr Phe Leu Arg
1190                1195                1200

Arg Pro Ile Asn Gln Val Val Leu Glu Glu Glu Ala Val Glu Phe
1205                1210                1215

Arg Cys Gln Val Gln Gly Asp Pro Gln Pro Thr Val Arg Trp Lys
1220                1225                1230

Lys Asp Asp Ala Asp Leu Pro Arg Gly Arg Tyr Asp Ile Lys Asp
1235                1240                1245

Asp Tyr Thr Leu Arg Ile Lys Lys Thr Met Ser Thr Asp Glu Gly
1250                1255                1260

Thr Tyr Met Cys Ile Ala Glu Asn Arg Val Gly Lys Met Glu Ala
1265                1270                1275

Ser Ala Thr Leu Thr Val Arg Ala Pro Pro Gln Phe Val Val Arg
1280                1285                1290

Pro Arg Asp Gln Ile Val Ala Gln Gly Arg Thr Val Thr Phe Pro
1295                1300                1305

Cys Glu Thr Lys Gly Asn Pro Gln Pro Ala Val Phe Trp Gln Lys
1310                1315                1320

Glu Gly Ser Gln Asn Leu Leu Phe Pro Asn Gln Pro Gln Gln Pro
1325                1330                1335

Asn Ser Arg Cys Ser Val Ser Pro Thr Gly Asp Leu Thr Ile Thr
1340                1345                1350

Asn Ile Gln Arg Ser Asp Ala Gly Tyr Tyr Ile Cys Gln Ala Leu
1355                1360                1365

Thr Val Ala Gly Ser Ile Leu Ala Lys Ala Gln Leu Glu Val Thr
1370                1375                1380

Asp Val Leu Thr Asp Arg Pro Pro Pro Ile Ile Leu Gln Gly Pro
1385                1390                1395

Ala Asn Gln Thr Leu Ala Val Asp Gly Thr Ala Leu Leu Lys Cys
1400                1405                1410

Lys Ala Thr Gly Asp Pro Leu Pro Val Ile Ser Trp Leu Lys Glu
1415                1420                1425

Gly Phe Thr Phe Pro Gly Arg Asp Pro Arg Ala Thr Ile Gln Glu
```

-continued

```
            1430               1435                1440

Gln Gly Thr Leu Gln Ile Lys Asn Leu Arg Ile Ser Asp Thr Gly
            1445               1450                1455

Thr Tyr Thr Cys Val Ala Thr Ser Ser Gly Glu Thr Ser Trp
            1460               1465                1470

Ser Ala Val Leu Asp Val Thr Glu Ser Gly Ala Thr Ile Ser Lys
            1475               1480                1485

Asn Tyr Asp Leu Ser Asp Leu Pro Gly Pro Pro Ser Lys Pro Gln
            1490               1495                1500

Val Thr Asp Val Thr Lys Asn Ser Val Thr Leu Ser Trp Gln Pro
            1505               1510                1515

Gly Thr Pro Gly Thr Leu Pro Ala Ser Ala Tyr Ile Ile Glu Ala
            1520               1525                1530

Phe Ser Gln Ser Val Ser Asn Ser Trp Gln Thr Val Ala Asn His
            1535               1540                1545

Val Lys Thr Thr Leu Tyr Thr Val Arg Gly Leu Arg Pro Asn Thr
            1550               1555                1560

Ile Tyr Leu Phe Met Val Arg Ala Ile Asn Pro Gln Gly Leu Ser
            1565               1570                1575

Asp Pro Ser Pro Met Ser Asp Pro Val Arg Thr Gln Asp Ile Ser
            1580               1585                1590

Pro Pro Ala Gln Gly Val Asp His Arg Gln Val Gln Lys Glu Leu
            1595               1600                1605

Gly Asp Val Leu Val Arg Leu His Asn Pro Val Val Leu Thr Pro
            1610               1615                1620

Thr Thr Val Gln Val Thr Trp Thr Val Asp Arg Gln Pro Gln Phe
            1625               1630                1635

Ile Gln Gly Tyr Arg Val Met Tyr Arg Gln Thr Ser Gly Leu Gln
            1640               1645                1650

Ala Thr Ser Ser Trp Gln Asn Leu Asp Ala Lys Val Pro Thr Glu
            1655               1660                1665

Arg Ser Ala Val Leu Val Asn Leu Lys Lys Gly Val Thr Tyr Glu
            1670               1675                1680

Ile Lys Val Arg Pro Tyr Phe Asn Glu Phe Gln Gly Met Asp Ser
            1685               1690                1695

Glu Ser Lys Thr Val Arg Thr Thr Glu Glu Ala Pro Ser Ala Pro
            1700               1705                1710

Pro Gln Ser Val Thr Val Leu Thr Val Gly Ser Tyr Asn Ser Thr
            1715               1720                1725

Ser Ile Ser Val Ser Trp Asp Pro Pro Pro Asp His Gln Asn
            1730               1735                1740

Gly Ile Ile Gln Glu Tyr Lys Ile Trp Cys Leu Gly Asn Glu Thr
            1745               1750                1755

Arg Phe His Ile Asn Lys Thr Val Asp Ala Ala Ile Arg Ser Val
            1760               1765                1770

Ile Ile Gly Gly Leu Phe Pro Gly Ile Gln Tyr Arg Val Glu Val
            1775               1780                1785

Ala Ala Ser Thr Ser Ala Gly Val Gly Val Lys Ser Glu Pro Gln
            1790               1795                1800

Pro Ile Ile Ile Gly Arg Arg Asn Glu Val Val Ile Thr Glu Asn
            1805               1810                1815

Asn Asn Ser Ile Thr Glu Gln Ile Thr Asp Val Val Lys Gln Pro
            1820               1825                1830
```

-continued

```
Ala Phe Ile Ala Gly Ile Gly Gly Ala Cys Trp Val Ile Leu Met
1835                1840                1845

Gly Phe Ser Ile Trp Leu Tyr Trp Arg Arg Lys Lys Arg Lys Gly
1850                1855                1860

Leu Ser Asn Tyr Ala Val Thr Phe Gln Arg Gly Asp Gly Gly Leu
1865                1870                1875

Met Ser Asn Gly Ser Arg Pro Gly Leu Leu Asn Ala Gly Asp Pro
1880                1885                1890

Ser Tyr Pro Trp Leu Ala Asp Ser Trp Pro Ala Thr Ser Leu Pro
1895                1900                1905

Val Asn Asn Ser Asn Ser Gly Pro Asn Glu Ile Gly Asn Phe Gly
1910                1915                1920

Arg Gly Asp Val Leu Pro Pro Val Pro Gly Gln Gly Asp Lys Thr
1925                1930                1935

Ala Thr Met Leu Ser Asp Gly Ala Ile Tyr Ser Ser Ile Asp Phe
1940                1945                1950

Thr Thr Lys Thr Ser Tyr Asn Ser Ser Ser Gln Ile Thr Gln Ala
1955                1960                1965

Thr Pro Tyr Ala Thr Thr Gln Ile Leu His Ser Asn Ser Ile His
1970                1975                1980

Glu Leu Ala Val Asp Leu Pro Asp Pro Gln Trp Lys Ser Ser Ile
1985                1990                1995

Gln Gln Lys Thr Asp Leu Met Gly Phe Gly Tyr Ser Leu Pro Asp
2000                2005                2010

Gln Asn Lys Gly Asn Asn Gly Gly Lys Gly Lys Lys Lys Lys Lys
2015                2020                2025

Asn Lys Asn Ser Ser Lys Pro Gln Lys Asn Asn Gly Ser Thr Trp
2030                2035                2040

Ala Asn Val Pro Leu Pro Pro Pro Val Gln Pro Leu Pro Gly
2045                2050                2055

Thr Glu Leu Glu His Tyr Ala Val Glu Gln Gln Glu Asn Gly Tyr
2060                2065                2070

Asp Ser Asp Ser Trp Cys Pro Pro Leu Pro Val Gln Thr Tyr Leu
2075                2080                2085

His Gln Gly Leu Glu Asp Glu Leu Glu Glu Asp Asp Arg Val
2090                2095                2100

Pro Thr Pro Pro Val Arg Gly Val Ala Ser Ser Pro Ala Ile Ser
2105                2110                2115

Phe Gly Gln Gln Ser Thr Ala Thr Leu Thr Pro Ser Pro Arg Glu
2120                2125                2130

Glu Met Gln Pro Met Leu Gln Ala His Leu Asp Glu Leu Thr Arg
2135                2140                2145

Ala Tyr Gln Phe Asp Ile Ala Lys Gln Thr Trp His Ile Gln Ser
2150                2155                2160

Asn Asn Gln Pro Pro Gln Pro Pro Val Pro Pro Leu Gly Tyr Val
2165                2170                2175

Ser Gly Ala Leu Ile Ser Asp Leu Glu Thr Asp Val Ala Asp Asp
2180                2185                2190

Asp Ala Asp Asp Glu Glu Glu Ala Leu Glu Ile Pro Arg Pro Leu
2195                2200                2205

Arg Ala Leu Asp Gln Thr Pro Gly Ser Ser Met Asp Asn Leu Asp
2210                2215                2220
```

| | | | | | | | | | | | |
|---|---|---|---|---|---|---|---|---|---|---|---|
| Ser | Ser | Val | Thr | Gly | Lys | Ala | Phe | Thr | Ser | Ser | Gln | Arg | Pro | Arg |
| | 2225 | | | | 2230 | | | | | 2235 | | | | |

Ser Ser Val Thr Gly Lys Ala Phe Thr Ser Ser Gln Arg Pro Arg
2225                2230                    2235

Pro Thr Ser Pro Phe Ser Thr Asp Ser Asn Thr Ser Ala Ala Leu
    2240                2245                    2250

Ser Gln Ser Gln Arg Pro Arg Pro Thr Lys Lys His Lys Gly Gly
2255                2260                    2265

Arg Met Asp Gln Gln Pro Ala Leu Pro His Arg Arg Glu Gly Met
    2270                2275                    2280

Thr Asp Glu Glu Ala Leu Val Pro Tyr Ser Lys Pro Ser Phe Pro
2285                2290                    2295

Ser Pro Gly Gly His Ser Ser Ser Gly Thr Ala Ser Ser Lys Gly
    2300                2305                    2310

Ser Thr Gly Pro Arg Lys Thr Glu Val Leu Arg Ala Gly His Gln
2315                2320                    2325

Arg Asn Ala Ser Asp Leu Leu Asp Ile Gly Tyr Met Gly Ser Asn
    2330                2335                    2340

Ser Gln Gly Gln Phe Thr Gly Glu Leu
2345                2350

```
<210> SEQ ID NO 2
<211> LENGTH: 7059
<212> TYPE: DNA
<213> ORGANISM: Homo sapiens

<400> SEQUENCE: 2
```

| | |
|---|---|
| atgacctcac ggacaaagcg aaggcagaaa gttaaaatca gcatatcgaa aataaatcac | 60 |
| tctagttacc gaaaagaaca taggccgttt tgggagcacc agccacctcc acaccagaac | 120 |
| tgggctgtcg ggggccgctg cggcgcaggg gctcgtccgg gactgagtca gcgccggggc | 180 |
| cgagaagttc ggcgggaggc gcagggcggg gcttcctccc gccgactccg agcccggctc | 240 |
| tactttctg agtccacgtc tcttcctttg acaggcgtg gcagcccggg ccgctcggc | 300 |
| ccagcccctc acggactgcg gcgcgcggct ccccggggcc cggcccgccg aacgcctcgc | 360 |
| tctacagccc tcacctcgcg gcgccgagcg cagcgtccgc ggcatggaga ccggctccga | 420 |
| ctcaggtcag aggcccgccc ccgggccgcg ggggactggc cctgcgcgcg cggcggcgcg | 480 |
| gttaggccgg gccgcccgca caggccgccg cgtgtcgagt ccgcgcgggg agcgcacgcg | 540 |
| gggcgggcgg cgacagatca gcttgaacgg gtcttttac gacttggcca tgctgaaaca | 600 |
| gatgaacaat tacagaatat tatatctaaa ttccttcctc ctgtttttgct caaactctct | 660 |
| agcacccaag aaggagtacg taaaaaggta atggaactgc tggtccatct gaataaacgt | 720 |
| ataaaaagcc gccccaaaat acaacttcca gtagagacac tgttggttca gtaccaggac | 780 |
| cctgctgcag tttcctttgt cacaaatttt actataattt atgttaaaat gggctatcct | 840 |
| cgcctaccag tggaaaaaca atgtgaactg cccctacgc ttcttactgc catggaaggg | 900 |
| aagcctcagc cacagcagga tagcttaatg catcttttaa taccaaccct ttttcacatg | 960 |
| aaataccctg ttgaatcatc aaaatcagct tctccattta atcttgctga aaaccaaag | 1020 |
| actgtgcagc tgcttttgga cttcatgcta gatgtcctc tgatgcctta tggttacgtg | 1080 |
| ttaaatgaat cccagagtcg ccaaaattca tcttcagcac agggttcttc ttcaaacagt | 1140 |
| ggcggaggtt ctggaatccc acagcctcct ccgggaatga gcttttatgc agccaaacga | 1200 |
| gttattggtg ataaccccatg gacacctgaa caattggaac agtgcaaatt gggaatcgtg | 1260 |
| aaattcatag aagctgaaca ggtgcctgaa cttgaagctg ttctccactt ggtgattgcc | 1320 |

-continued

```
tctagtgata cacgccacag tgtggcaacg gcagcagacc tggaattgaa aagcaaacag    1380
agcttaattg actggaataa tcctgccatc attaataaga gtacaaggt gtaccttgga     1440 gatataccac tgaagacaaa agagggtgca gttctgaagc cagagttgaa aagggaccct   1500
gtcagtacaa gagtcaagtt aaagattgtc ccccatctcc tccgctctag acaagctgct   1560
gaaacgttcc cagccaacat tcaggtggtg tatgatggac ttttggtac aaatacaaat    1620 tcaaagttaa gaacattatc cctgcaattt gtgcatcata tttgtataac ctgtccagaa   1680
atcaagatta agccattagg tccaatgctt ttgaatggcc tcaccaagct aatcaatgaa   1740
tacaaagagg accctaaact actgtcaatg gcatattcag ctgttggaaa actctccagt   1800
cggatgccac atttattcac taaggatata gcgcttgtgc agcagctttt tgaagccctt   1860
tgcaaggaag agcctgagac tcgacttgct attcaagaag ctttatctat gatggttgga   1920
gcgtatagta ctttggaagg ggcacagcga actctcatgg aggcacttgt ggcttcgtac   1980
ttaataaagc ctgaagttca agttcgacaa gtggctgtga aatttgccag tacggtgttt   2040
ccctcagatc atatcccttc cagatatttg ctgctactgg ctgcaggaga tccacgtgaa   2100
gaagttcatg gagaagcaca acgcgtatta aggtgtcttc caggtagaaa cagaaaagaa   2160
agtacttctg agcagatgcc ttccttccca gaaatggttt attacatcca agaaaaggct   2220
tctcatcgaa tgaaaactcc agtcaagtac atgaccggga ccactgtcct tccatttaac   2280
ccagcagcct ttggagagat cgttctgtac ttgcgcatgt gccttgcgca cagtgcgggg   2340
gtggtgccca cctctcagag tttggctgat atgcaggatc atgccccagc cattgggcgc   2400
tacatacgga ctttaatgtc aagcgggcag atggcaccct catcatctaa caagagtggg   2460
gagactaacc ctgtccagat ctacattggc ctgcttcagc agctgttagc aggtgttgga   2520
ggtttgccgg ttatgtactg tctattggaa gctgtgtcag tgtatccaga aaagctggct   2580
accaaatttg tagacaaaac agaatggata aagagtctga tgaataacag taaagaagaa   2640
atgcgcgaac tggcagcgtt gttttattct gtagtggtat caacagtgtc ggggaatgag   2700
ttgaaatcaa tgatagaaca gcttataaag actacaaaag acaatcacag cccggagata   2760
cagcatggat ccttgcttgc attgggattc acgtgtggaa ggtatttggc taaaaagaaa   2820
atgagaatgt cagagcaaca agacctggag agaaatgctg acaccctccc tgatcaagag   2880
gaactcattc agagtgctac agaaacaata ggctcatttt tggacagtac atcccctc    2940 ctggcaattg ctgcctgcac agccctgggt gaaattggca gaaatggtcc acttccaatc   3000
cccagtgagg gatctggctt taccaaattg catcttgtag aaagcttact aagtagaata   3060
ccttccagta agaaacaaa taagatgaaa gaacgagcaa tccaaacact gggatatttt   3120
ccagttgggg atggagattt tcctcaccag aaactcctct tgcaaggtct gatggattct   3180
gtggaggcca agcagataga acttcagttc actattggcg aagccattac cagtgctgca   3240
ataggaacta gttctgtggc tgcccgagat gcctggcaaa tgactgaaga ggaatatact   3300
ccacctgctg tgttacgaga tgacttccga caaaacccca cagatgttgt agtggcagct   3360
ggagagcctg caatcctgga gtgccagcct ccccggggac acccagaacc caccatctac   3420
tggaaaaaag acaagttcg aattgatgac aaggaagaaa gaataagtat ccgtggtgga   3480
aaactgatga tctccaatac caggaaaagt gatgcaggga tgtatacttg tgttggtacc   3540
aatatggtgg gagaaaggga cagtgaccca gcagagctga ctgtctttga acgacccaca   3600
tttctcagga ggccaattaa ccaggtggta ctggaggaag aagctgtaga atttcgttgt   3660
caagtccaag gagatcctca accaactgtg aggtggaaaa aggatgatgc agacttgcca   3720
```

```
agaggaaggt atgacatcaa agacgattac acactaagaa ttaaaaagac catgagtaca    3780
gatgaaggca cctatatgtg tattgctgag aatcgggttg gaaaaatgga agcctctgct    3840
acactcaccg tccgagctcc cccacagttt gtggttcggc aagagatca gattgttgct     3900 caaggtcgaa cagtgacatt tccctgtgaa actaaaggaa acccacagcc agctgttttt    3960
tggcagaaag aaggcagcca gaacctactt ttcccaaacc aaccccagca gcccaacagt    4020
agatgctcag tgtcaccaac tggagacctc acaatcacca acattcaacg ttccgacgcg    4080
ggttactaca tctgccaggc tttaactgtg gcaggaagca ttttagcaaa agctcaactg    4140
gaggttacta atgttttgac agatagacct ccacctataa ttctacaagg cccagccaac    4200
caaacgctgg cagtggatgg tacagcgtta ctgaaatgta aagccactgg tgatcctctt    4260
cctgtaatta gctggttaaa ggagggattt acttttccgg gtagagatcc aagagcaaca    4320
attcaagagc aaggcacact gcagattaag aatttacgga tttctgatac tggcacttat    4380
acttgtgtgg ctacaagttc aagtggagag acttcctgga gtgcagtgct ggatgtgaca    4440
gagtctggag caacaatcag taaaaactat gatttaagtg acctgccagg gccaccatcc    4500
aaaccgcagg tcactgatgt tactaagaac agtgtcacct tgtcctggca gccaggtacc    4560
cctggaaccc ttccagcaag tgcatatatc attgaggctt cagccaatc agtgagcaac     4620 agctggcaga ccgtggcaaa ccatgtaaag accaccctct atactgtaag aggactgcgg    4680
cccaatacaa tctacttatt catggtcaga gcgatcaacc cccaaggtct cagtgaccca    4740
agtcccatgt cagatcctgt gcgcacacaa gatatcagcc caccagcaca aggagtggac    4800
cacaggcaag tgcagaaaga gctaggagat gtccttgtcc gtcttcataa tccagttgtg    4860
ctgactccca ccacggttca ggtcacatgg acggttgatc gccaaccca gtttatccaa     4920 ggctaccgag tgatgtatcg tcagacttca ggtctgcagg cgacatcttc gtggcagaat    4980
ttagatgcca aagtcccgac tgaacgaagt gctgtcttag tcaacctgaa aaaggggtg     5040 acttatgaaa ttaaagtacg gccatatttt aatgagttcc aaggaatgga tagtgaatct    5100
aaaacggttc gtactactga agaagcccca agtgccccac cacagtctgt cactgtactg    5160
acagttggaa gctacaatag cacaagtatt agtgtttcct gggatcctcc tcctccagat    5220
caccagaatg gaattatcca agaatacaag atctggtgtc taggaaatga aacgcgattc    5280
catatcaaca aaactgtgga tgcagccatt cggtccgtaa taattggtgg attattccca    5340
ggtattcaat accgggtaga ggttgcagct agtaccagtg caggggttgg agtaaagagt    5400
gagccacagc caataataat cgggagacgc aatgaagttg tcattactga aaacaataac    5460
agcataactg agcaaatcac tgatgtggtg aagcaaccag cctttatagc tggtattggt    5520
ggtgcctgct gggtaattct gatgggtttt agcatatggt tgtattggcg aagaaagaag    5580
aggaagggac tcagtaatta tgctgttacg tttcaaagag gagatggagg actaatgagc    5640 aatgaagcc gtccaggtct tctcaatgct ggtgatccca gctatccatg gcttgctgat    5700
tcttggccag ccacgagctt gccagtaaat aatagcaaca gtggcccaaa tgagattgga    5760
aattttggcc gtggagatgt gctgccacca gttccaggcc aagggataa acagcaacg     5820 atgctctcag atggagccat ttatagtagc attgacttca ctaccaaaac cagttacaac    5880
agttccagcc aaataacaca ggctacccca tatgccacga cacagatctt gcattccaac    5940
agcatacatg aattggctgt cgatctgcct gatccacaat ggaaaagctc aattcagcaa    6000
aaaacagatc tgatgggatt tggttattct ctacctgatc agaacaaagg taacaatggt    6060
```

| | |
|---|---|
| gggaaaggtg gaaaaagaa gaaaaataaa aactcttcta aaccacagaa aaacaatgga | 6120 |
| tccacttggg ccaatgtccc tctacctccc ccccagtcc agccccttcc tggcacggag | 6180 |
| ctggaacact atgcagtgga caacaagaa aatggctatg acagtgatag ctggtgccca | 6240 |
| ccattgccag tacaaactta cttacaccaa ggtctggaag atgaactgga agaagatgat | 6300 |
| gatagggtcc caacacctcc tgttcgaggc gtggcttctt ctcctgctat ctcctttgga | 6360 |
| cagcagtcca ctgcaactct tactccatcc ccacgggaag agatgcaacc catgctgcag | 6420 |
| gctcacctgg atgagttgac aagagcctat cagtttgata tagcaaaaca aacatggcac | 6480 |
| attcaaagca ataatcaacc tccacagcct ccagttccac cgttaggtta tgtgtctgga | 6540 |
| gccttgattt ctgatttgga aacggatgtt gcagatgatg atgccgacga cgaagaggaa | 6600 |
| gctttagaaa tccccaggcc cctgagagca ctggaccaga ctcctggatc cagcatggac | 6660 |
| aatctagaca gctctgtgac aggaaaagcc tttacctcct ctcaaagacc tcgacctacc | 6720 |
| agcccatttt ctactgacag taacaccagt gcagccctga gtcaaagtca gaggcctcgg | 6780 |
| cccactaaaa aacacaaggg agggcggatg gaccaacaac cagcattgcc tcatcgaagg | 6840 |
| gaaggaatga cagatgagga ggccttggtg ccctatagca agcccagttt cccatctcca | 6900 |
| ggtggccaca gctcatcagg aacagcttct tctaagggat ccactggacc taggaaaaacc | 6960 |
| gaggtgttga gagcaggcca ccagcgcaat gccagcgacc ttcttgacat aggatatatg | 7020 |
| ggctccaaca gtcaaggaca gtttacaggt gaattatag | 7059 |

<210> SEQ ID NO 3
<211> LENGTH: 3310
<212> TYPE: DNA
<213> ORGANISM: Homo sapiens

<400> SEQUENCE: 3

| | |
|---|---|
| atgacctcac ggacaaagcg aaggcagaaa gttaaaatca gcatatcgaa ataaatcac | 60 |
| tctagttacc gaaagaaca taggccgttt tgggagcacc agccacctcc acaccagaac | 120 |
| tgggctgtcg ggggccgctg cggcgcaggg gctcgtccgg gactgagtca gcgccggggc | 180 |
| cgagaagttc ggcgggaggc gcagggcggg gcttcctccc gccgactccg agcccggctc | 240 |
| tactttctg agtccacgtc tcttcctttg dacaggcgtg gcagcccggg cccgctcggc | 300 |
| ccagcccctc acggactgcg gcgccgcggct ccccggggcc cggcccgccg aacgcctcgc | 360 |
| tctacagccc tcacctcgcg gcgccgagcg cagcgtccgc ggcatggaga ccggctccga | 420 |
| ctcaggtcag aggcccgccc ccgggccgcg ggggactggc cctgcgcgcg cggcggcgcg | 480 |
| gttaggccgg gccgcccgca caggccgccg cgtgtcgagt ccgcgcgggg agcgcacgcg | 540 |
| gggcgggcgg cgacagatca gcttgaacgg gtcttttttac gacttggcca tgctgaaaca | 600 |
| gatgaacaat tacagaatat tatatctaaa ttccttcctc ctgttttgct caaactctct | 660 |
| agcacccaag aaggagtacg taaaaaggta atggaactgc tggtccatct gaataaacgt | 720 |
| ataaaaagcc gccccaaaat acaacttcca gtagagacac tgttggttca gtaccaggac | 780 |
| cctgctgcag tttccttttgt cacaaatttt actataattt atgttaaaat gggctatcct | 840 |
| cgcctaccag tggaaaaaca atgtgaactg gcccctacgc ttcttactgc catggaaggg | 900 |
| aagcctcagc cacagcagga tagcttaatg catctttaa taccaaccct ttttcacatg | 960 |
| aaatacccctg ttgaatcatc aaaatcagct tctccattta atcttgctga gaaaccaaag | 1020 |
| actgtgcagc tgcttttgga cttcatgcta gatgtccttc tgatgcctta tggttacgtg | 1080 |
| ttaaatgaat cccagagtcg ccaaaattca tcttcagcac agggttcttc ttcaaacagt | 1140 |

```
ggcggaggtt ctggaatccc acagcctcct ccgggaatga gcttttatgc agccaaacga    1200
gttattggtg ataacccatg acacctgaa caattggaac agtgcaaatt gggaatcgtg     1260
aaattcatag aagctgaaca ggtgcctgaa cttgaagctg ttctccactt ggtgattgcc    1320
tctagtgata cacgccacag tgtggcaacg gcagcagacc tggaattgaa aagcaaacag    1380
agcttaattg actggaataa tcctgccatc attaataaga tgtacaaggt gtaccttgga    1440
gatataccac tgaagacaaa agagggtgca gttctgaagc cagagttgaa aagggaccct    1500
gtcagtacaa gagtcaagtt aaagattgtc ccccatctcc tccgctctag acaagctgct    1560
gaaacgttcc cagccaacat tcaggtggtg tatgatggac ttttttggtac aaatacaaat   1620 tcaaagttaa gaacattatc cctgcaattt gtgcatcata tttgtataac ctgtccagaa    1680
atcaagatta agccattagg tccaatgctt ttgaatggcc tcaccaagct aatcaatgaa    1740
tacaaagagg accctaaact actgtcaatg gcatattcag ctgttggaaa actctccagt    1800
cggatgccac atttattcac taaggatata gcgcttgtgc agcagctttt tgaagccctt    1860
tgcaaggaag agcctgagac tcgacttgct attcaagaag ctttatctat gatggttgga    1920
gcgtatagta ctttggaagg ggcacagcga actctcatgg aggcacttgt ggcttcgtac    1980
ttaataaagc ctgaagttca agttcgacaa gtggctgtga aatttgccag tacggtgttt    2040
ccctcagatc atatcccttc cagatatttg ctgctactgg ctgcaggaga tccacgtgaa    2100
gaagttcatg gagaagcaca acgcgtatta aggtgtcttc caggtagaaa cagaaaagaa    2160
agtacttctg agcagatgcc ttccttccca gaaatggttt attacatcca agaaaaggct    2220
tctcatcgaa tgaaaactcc agtcaagtac atgaccggga ccactgtcct tccatttaac    2280
ccagcagcct ttggagagat cgttctgtac ttgcgcatgt gccttgcgca cagtgcgggg    2340
gtggtgccca cctctcagag tttggctgat atgcaggatc atgccccagc cattgggcgc    2400
tacatacgga ctttaatgtc aagcgggcag atggcaccct catcatctaa caagagtggg    2460
gagactaacc ctgtccagat ctacattggc ctgcttcagc agctgttagc aggtgttgga    2520
ggtttgccgg ttatgtactg tctattggaa gctgtgtcag tgtatccaga aaagctggct    2580
accaaatttg tagacaaaac agaatggata aagagtctga tgaataacag taagaagaa     2640 atgcgcgaac tggcagcgtt gttttattct gtagtggtat caacagtgtc ggggaatgag    2700
ttgaaatcaa tgatagaaca gcttataaag actacaaaag acaatcacag cccggagata    2760
cagcatggat ccttgcttgc attgggattc acggtgggaa ggtatttggc taaaagaaa    2820 atgagaatgt cagagcaaca agacctggag agaaatgctg acaccctccc tgatcaagag    2880
gaactcattc agagtgctac agaaacaata ggctcatttt tggacagtac atcacccctc    2940
ctggcaattg ctgcctgcac agccctgggt gaaattggca gaatggtcc acttccaatc     3000 cccagtgagg gatctggctt taccaaattg catcttgtag aaagcttact aagtagaata    3060
ccttccagta aagaaacaaa taagatgaaa gaacgagcaa tccaaacact gggatatttt    3120
ccagttgggg atggagattt tcctcaccag aaactcctct gcaaggtct gatggattct     3180 gtggaggcca agcagataga acttcagttc actattggcg aagccattac cagtgctgca    3240
ataggaacta gttctgtggc tgcccgagat gcctggcaaa tgactgaaga ggaatatact    3300
ccacctgctg                                                          3310
```

<210> SEQ ID NO 4
<211> LENGTH: 3749
<212> TYPE: DNA

<213> ORGANISM: Homo sapiens

<400> SEQUENCE: 4

| | | | | | |
|---|---|---|---|---|---|
| tgttacgaga | tgacttccga | caaaacccca | cagatgttgt | agtggcagct | ggagagcctg | 60 |
| caatcctgga | gtgccagcct | ccccggggac | acccagaacc | caccatctac | tggaaaaaag | 120 |
| acaaagttcg | aattgatgac | aaggaagaaa | gaataagtat | ccgtggtgga | aaactgatga | 180 |
| tctccaatac | caggaaaagt | gatgcaggga | tgtatacttg | tgttggtacc | aatatggtgg | 240 |
| gagaaaggga | cagtgaccca | gcagagctga | ctgtctttga | acgacccaca | tttctcagga | 300 |
| ggccaattaa | ccaggtggta | ctggaggaag | aagctgtaga | atttcgttgt | caagtccaag | 360 |
| gagatcctca | accaactgtg | aggtggaaaa | aggatgatgc | agacttgcca | agaggaaggt | 420 |
| atgacatcaa | agacgattac | acactaagaa | ttaaaaagac | catgagtaca | gatgaaggca | 480 |
| cctatatgtg | tattgctgag | aatcgggttg | gaaaaatgga | agcctctgct | acactcaccg | 540 |
| tccgagctcc | cccacagttt | gtggttcggc | caagagatca | gattgttgct | caaggtcgaa | 600 |
| cagtgacatt | tccctgtgaa | actaaaggaa | acccacagcc | agctgttttt | tggcagaaag | 660 |
| aaggcagcca | gaacctactt | ttcccaaacc | aaccccagca | gcccaacagt | agatgctcag | 720 |
| tgtcaccaac | tggagacctc | acaatcacca | acattcaacg | ttccgacgcg | ggttactaca | 780 |
| tctgccaggc | tttaactgtg | gcaggaagca | ttttagcaaa | agctcaactg | gaggttactg | 840 |
| atgttttgac | agatagacct | ccacctataa | ttctacaagg | cccagccaac | caaacgctgg | 900 |
| cagtggatgg | tacagcgtta | ctgaaatgta | aagccactgg | tgatcctctt | cctgtaatta | 960 |
| gctggttaaa | ggagggattt | acttttccgg | gtagagatcc | aagagcaaca | attcaagagc | 1020 |
| aaggcacact | gcagattaag | aatttacgga | tttctgatac | tggcacttat | acttgtgtgg | 1080 |
| ctacaagttc | aagtgggagag | acttcctgga | gtgcagtgct | ggatgtgaca | gagtctggag | 1140 |
| caacaatcag | taaaaactat | gatttaagtg | acctgccagg | gccaccatcc | aaaccgcagg | 1200 |
| tcactgatgt | tactaagaac | agtgtcacct | tgtcctggca | gccaggtacc | cctggaaccc | 1260 |
| ttccagcaag | tgcatatatc | attgaggctt | tcagccaatc | agtgagcaac | agctggcaga | 1320 |
| ccgtggcaaa | ccatgtaaag | accaccctct | atactgtaag | aggactgcgg | cccaatacaa | 1380 |
| tctacttatt | catggtcaga | gcgatcaacc | cccaaggtct | cagtgaccca | agtcccatgt | 1440 |
| cagatcctgt | gcgcacacaa | gatatcagcc | caccagcaca | aggagtggac | cacaggcaag | 1500 |
| tgcagaaaga | gctaggagat | gtccttgtcc | gtcttcataa | tccagttgtg | ctgactccca | 1560 |
| ccacggttca | ggtcacatgg | acggttgatc | gccaaccca | gtttatccaa | ggctaccgag | 1620 |
| tgatgtatcg | tcagacttca | ggtctgcagg | cgacatcttc | gtggcagaat | ttagatgcca | 1680 |
| aagtcccgac | tgaacgaagt | gctgtcttag | tcaacctgaa | aaaggggtg | acttatgaaa | 1740 |
| ttaaagtacg | gccatatttt | aatgagttcc | aaggaatgga | tagtgaatct | aaaacggttc | 1800 |
| gtactactga | agaagcccca | agtgccccac | cacagtctgt | cactgtactg | acagttggaa | 1860 |
| gctacaatag | cacaagtatt | agtgtttcct | gggatcctcc | tcctccagat | caccagaatg | 1920 |
| gaattatcca | agaatacaag | atctggtgtc | taggaaatga | aacgcgattc | catatcaaca | 1980 |
| aaactgtgga | tgcagccatt | cggtccgtaa | taattgtgg | attattccca | ggtattcaat | 2040 |
| accgggtaga | ggttgcagct | agtaccagtg | caggggttgg | agtaaagagt | gagccacagc | 2100 |
| caataataat | cgggagacgc | aatgaagttg | tcattactga | aaacaataac | agcataactg | 2160 |
| agcaaatcac | tgatgtggtg | aagcaaccag | cctttatagc | tggtattggt | ggtgcctgct | 2220 |
| gggtaattct | gatgggtttt | agcatatggt | tgtattggcg | aagaaagaag | aggaagggac | 2280 |

-continued

```
tcagtaatta tgctgttacg tttcaaagag gagatggagg actaatgagc aatggaagcc    2340
gtccaggtct tctcaatgct ggtgatccca gctatccatg gcttgctgat tcttggccag    2400
ccacgagctt gccagtaaat aatagcaaca gtggcccaaa tgagattgga aattttggcc    2460
gtggagatgt gctgccacca gttccaggcc aaggggataa aacagcaacg atgctctcag    2520
atggagccat ttatagtagc attgacttca ctaccaaaac cagttacaac agttccagcc    2580
aaataacaca ggctaccca tatgccacga cacagatctt gcattccaac agcatacatg    2640
aattggctgt cgatctgcct gatccacaat ggaaaagctc aattcagcaa aaaacagatc    2700
tgatgggatt tggttattct ctacctgatc agaacaaagg taacaatggt gggaaaggtg    2760
gaaaaagaa gaaaaataaa aactcttcta aaccacagaa aaacaatgga tccacttggg    2820
ccaatgtccc tctacctccc cccccagtcc agccccttcc tggcacggag ctggaacact    2880
atgcagtgga acaacaagaa aatggctatg acagtgatag ctggtgccca ccattgccag    2940
tacaaactta cttacaccaa ggtctggaag atgaactgga agaagatgat gatagggtcc    3000
caacacctcc tgttcgaggc gtggcttctt ctcctgctat ctcctttgga cagcagtcca    3060
ctgcaactct tactccatcc ccacgggaag agatgcaacc catgctgcag gctcacctgg    3120
atgagttgac aagagcctat cagtttgata tagcaaaaca aacatggcac attcaaagca    3180
ataatcaacc tccacagcct ccagttccac cgttaggtta tgtgtctgga gccttgattt    3240
ctgatttgga aacggatgtt gcagatgatg atgccgacga cgaagaggaa gctttagaaa    3300
tccccaggcc cctgagagca ctggaccaga ctcctggatc cagcatggac aatctagaca    3360
gctctgtgac aggaaaagcc tttacctcct ctcaaagacc tcgacctacc agcccatttt    3420
ctactgacag taacaccagt gcagccctga gtcaaagtca gaggcctcgg cccactaaaa    3480
aacacaaggg agggcggatg gaccaacaac cagcattgcc tcatcgaagg gaaggaatga    3540
cagatgagga ggccttggtg ccctatagca agcccagttt cccatctcca ggtggccaca    3600
gctcatcagg aacagcttct tctaagggat ccactggacc taggaaaaacc gaggtgttga    3660
gagcaggcca ccagcgcaat gccagcgacc ttcttgacat aggatatatg ggctccaaca    3720
gtcaaggaca gtttacaggt gaattatag                                      3749
```

<210> SEQ ID NO 5
<211> LENGTH: 20
<212> TYPE: DNA
<213> ORGANISM: Artificial sequence
<220> FEATURE:
<223> OTHER INFORMATION: PCR primer

<400> SEQUENCE: 5
gcagacttgc caagaggaag    20

<210> SEQ ID NO 6
<211> LENGTH: 20
<212> TYPE: DNA
<213> ORGANISM: Artificial sequence
<220> FEATURE:
<223> OTHER INFORMATION: PCR primer

<400> SEQUENCE: 6
ttttccaacc cgattctcag    20

<210> SEQ ID NO 7
<211> LENGTH: 20
<212> TYPE: DNA

```
<213> ORGANISM: Artificial sequene
<220> FEATURE:
<223> OTHER INFORMATION: PCR primer

<400> SEQUENCE: 7
ttggattgct cgttctttca                                                    20

<210> SEQ ID NO 8
<211> LENGTH: 20
<212> TYPE: DNA
<213> ORGANISM: Artificial sequence
<220> FEATURE:
<223> OTHER INFORMATION: PCR primer

<400> SEQUENCE: 8
tgagggatct ggctttacca                                                    20
```